(12) United States Patent
Bazhenov et al.

(10) Patent No.: US 10,967,181 B2
(45) Date of Patent: Apr. 6, 2021

(54) APPARATUS AND METHODS FOR ESTIMATING AN ELECTRICAL STIMULATION EFFECT ON CORTICAL NEURONS

(71) Applicant: The Regents of the University of California, Oakland, CA (US)

(72) Inventors: Maksim Bazhenov, San Diego, CA (US); Eric Halgren, La Jolla, CA (US); Maxim Komarov, Oakland, CA (US); Paola Malerba, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 129 days.

(21) Appl. No.: 16/162,352

(22) Filed: Oct. 16, 2018

(65) Prior Publication Data

US 2019/0111257 A1 Apr. 18, 2019

Related U.S. Application Data

(60) Provisional application No. 62/573,129, filed on Oct. 16, 2017.

(51) Int. Cl.
*A61N 1/36* (2006.01)
*A61N 1/05* (2006.01)

(52) U.S. Cl.
CPC ....... *A61N 1/36025* (2013.01); *A61N 1/0531* (2013.01); *A61N 1/0534* (2013.01); *A61N 1/36185* (2013.01); *A61N 1/36082* (2013.01)

(58) Field of Classification Search
CPC .............. A61N 1/36025; A61N 1/0531; A61N 1/0534; A61N 1/36185; A61N 1/36082
USPC ......................................... 607/2, 4; 600/544
See application file for complete search history.

(56) References Cited

U.S. PATENT DOCUMENTS

| | | | | |
|---|---|---|---|---|
| 8,180,601 | B2* | 5/2012 | Butson | A61B 5/7257 703/2 |
| 8,494,627 | B2* | 7/2013 | Bikson | A61N 1/0456 607/2 |
| 2004/0158298 | A1* | 8/2004 | Gliner | A61N 1/36021 607/48 |

* cited by examiner

*Primary Examiner* — Carl H Layno
*Assistant Examiner* — Anh-Khoa N Dinh
(74) *Attorney, Agent, or Firm* — Sheppard, Mullin, Richter & Hampton LLP

(57) ABSTRACT

A method is disclosed for predicting the stimulation effect of cortical neurons in response to extracellular electrical stimulation. The method comprising the steps of defining an electrode configuration, defining a reconstructed neuronal cell type, wherein the reconstructed neuronal cell is characteristic of the physical and electrical properties of a neuronal cell, computing an electric field potential at the reconstructed neuronal cell, computing an effective transmembrane current of an arborization of the reconstructed neuronal cell, and determining a probability of activation of the reconstructed neuronal cell. A method for inducing an electrical stimulation effect on a cortical column is also disclosed. In an embodiment, the predicted network response of a cortical column is used to configure one or more electrodes to induce cortical stimulation.

18 Claims, 17 Drawing Sheets

APPARATUS AND METHODS FOR ESTIMATING AN ELECTRICAL STIMULATION EFFECT ON CORTICAL NEURONS

RELATED APPLICATIONS

This application claims the benefit of U.S. Provisional Patent Application No. 62/573,129, filed on Oct. 16, 2017, the contents of which is incorporated herein by reference in its entirety.

TECHNICAL FIELD

The present disclosure generally relates to cortical neurons. In particular, some embodiments of the present disclosure relate to predicting the stimulation effect of cortical neurons in response to extracellular electrical stimulation.

INTRODUCTION

Brain stimulation is widely used for a variety of reasons. Some of these reasons may include probing the neural system to learn about its properties, to normalize dysfunction (e.g., deep brain stimulation for Parkinsonian patients and direct-current stimulation for stroke and epileptic patients), to manipulate brain activity (including for including enhancing memories and learning), and for other purposes. The practice of brain stimulation is widespread and scalable. Brain stimulation may be accomplished, for example, through a range of instrumentalities from using electrode plates on the skull to using electrode arrays implanted intracranially in humans and animals. However, medical professionals still operate at a level of trial and error when attempting to predict the effects of electrical stimulation corresponding to a select region of the brain tissue. This is because predicting the effect of electrical stimulation on brain tissue with any degree of specificity is extremely difficult. In particular, it is not known which cells, if any, will react to an input, and which specific synaptic mechanisms will be recruited and modulated by a given stimulation protocol. Furthermore, depending on the goal of stimulation, the interesting effect could be driving cells to spike or inducing sub-threshold changes. Experimentally, stimulation can synchronize, de-synchronize, excite or suppress neuronal activity. But the bridge connecting the overall observations to cortical anatomy and the physics of current fields has proven hard to build.

Research efforts in this field have attempted to define the specifics of current flow when a cortical electrode delivers current to brain tissue. In particular, anatomical measures derived from brain scans, cell reconstructions, and other measures have been used to populate finite element models, leading to patient-specific suggestions regarding where current would flow for a given electrode placement. This approach typically requires large and detailed models of brain tissue, extending at times to the entire brain. Such models are often passive, meaning the active properties of neurons (e.g., the ability to spike, the synaptic dynamics, the intrinsic—potentially resonant—membrane currents) are not taken into account. More generally, measuring the effect of micro-stimulation implies combining multiple techniques such as optical imaging and electrophysiology. Each of these techniques typically has its own limitations in temporal and spatial resolution. In fact, differential recruitment within layers has been at the root of recent debate on whether electrical micro-stimulation leads to focal or distributed cell activation. Ideally, one would like to see the entire cortical volume below an electrode and image spiking and membrane potentials across layers and cell types.

BRIEF DESCRIPTION OF THE DRAWINGS

Various embodiments are disclosed herein and described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

Figure 1:
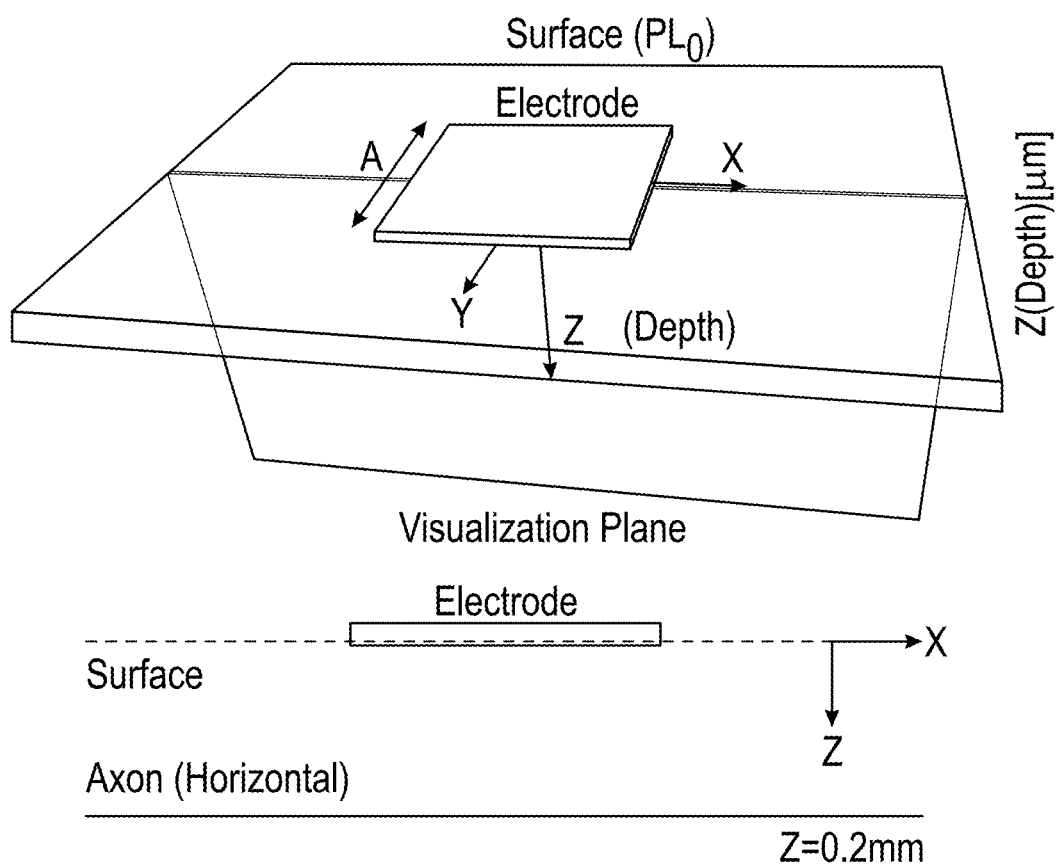
FIG. 1 illustrates an electric potential under an electrode plate and its effect on axonal fibers in accordance with various embodiments of the present disclosure.

The figures are not intended to be exhaustive or to limit the invention to the precise form disclosed. It should be understood that the invention can be practiced with modification and alteration, and that the disclosed technology be limited only by the claims and the equivalents thereof.

SUMMARY OF THE INVENTION

Various embodiments of the technologies disclosed herein describe a method for inducing an electrical stimulation effect on a cortical column. In one embodiment, the method comprises: estimating an electric field potential in the cortical column to be stimulated, wherein the cortical column is represented by a reconstructed neuronal cell; defining a reconstructed neuronal cell type for the reconstructed neuronal cell; defining an axonal-electrical receptive field based on at least the reconstructed neuronal cell type located in a cortical layer of the cortical column; estimating a probability of activation for the reconstructed neuronal cell based on at least the value of an activation function in axonal elements of the reconstructed neuronal cell; predicting a network response to electrical stimulation based on at least the probability of activation estimate for the reconstructed neuronal cell; and using at least the predicted network response to configure a physical electrode relative to the cortical column to stimulate the cortical column.

In one implementation, the cortical column may be stimulated by the physical electrode to generate a response corresponding to the predicted network response. The stimulation may be either cathodal or anodal stimulation. In another embodiment, the cell may be represented by the equation:

$$f = \frac{d}{4\rho_i} \frac{\partial^2 \Phi}{\partial x^2}$$

where x represents the direction of an axonal fiber; $\Phi$ is a function representing extracellular potentials in the vicinity of axonal compartments; and $\rho_i$ represents a resistivity of axoplasm.

In some implementations, the defined reconstructed neuronal cell type may comprise a physical property or an electrical property of the reconstructed neuronal cell. The reconstructed neuronal cell type may comprise pyramidal cells, excitatory spiny stellate cells, basket cells, Martinotti cells, and bi-tufted interneurons.

In various implementations, the method may be directed to inducing a desired brain response based on the polar state of a reconstructed neuronal cell. For example, the method may comprise: estimating a probability of depolarization or hyperpolarization of the reconstructed neuronal cell; predicting a network polarization response to electrical stimulation based on at least the estimated probability of depolarization or hyperpolarization the reconstructed neuronal cell; and using at least the predicted network polarization response to configure the physical electrode relative to the cortical column to stimulate the cortical column.

In some embodiments, the a non-transitory computer-readable medium having executable instructions stored thereon that, when executed by a processor, may perform the operations of: defining an electrode configuration of an electrode, wherein the electrode stimulates a reconstructed neuronal cell; defining a reconstructed neuronal cell type for the reconstructed neuronal cell; computing an electric field potential at the reconstructed neuronal cell due to the electrode using at least the defined electrode configuration; computing an effective transmembrane current of an arborization of the reconstructed neuronal cell using at least the computed electric field potential; and determining a probability of activation of the reconstructed neuronal cell using at least the computed effective transmembrane current and the defined reconstructed neuronal cell type.

In particular implementations, a probability of activation may be determined for multiple reconstructed neuronal cells. For example, the non-transitory computer-readable medium may comprise instructions, that when executed by the processor, further perform the operations of: determining the probability of activation for multiple reconstructed neuronal cells in a brain region according to the methods disclosed herein, wherein the multiple reconstructed neuronal cells each have a respective reconstructed neuronal cell type. Further, various embodiments may use statistical inference to predict an average response in a brain region for the multiple reconstructed neuronal cells.

In some embodiments, the electrode configuration may comprise specifying a size, shape, and current output of the electrode. Further, the defined reconstructed neuronal cell type may comprises a physical property or an electrical property of the reconstructed neuronal cell, wherein a physical property comprises an average axonal density of the reconstructed neuronal cell.

In particular implementations, the polarity of the effective transmembrane current may be used to determine the probability of activation of the reconstructed neuronal cell.

In various embodiments, the effective transmembrane current may be described by the equation:

$$f = \frac{d}{4\rho_i} \frac{\Phi_{i-1} - 2\Phi_i + \Phi_{i+1}}{\Delta x^2},$$

where $\Phi_i$, $\Phi_{i-1}$, and $\Phi_{i+1}$ represent extracellular potentials in the vicinity of an axonal compartment; d represents an axonal diameter; $\rho_1$ represents a resistivity of axoplasm; and $\Delta x$ is a discretization parameter, which defines length of the axonal compartment. In some embodiments, the reconstructed neuronal cell type may comprise one or more of pyramidal cells, excitatory spiny stellate cells, basket cells, Martinotti cells, and bi-tufted interneurons. In one embodiment, the non-transitory computer-readable media may comprise instructions, wherein the instructions, when executed by a processor, calculate a probability of depolarization or hyperpolarization of the reconstructed neuronal cell.

Various embodiments of the technologies disclosed herein describe a method of computing a probability of neuronal cell activation. The method may comprise: defining an electrode configuration of an electrode, wherein the electrode stimulates a reconstructed neuronal cell; computing an electric field potential at a position (R,Z) of the reconstructed neuronal cell relative to the electrode, wherein R is the planar distance from the center of the electrode and Z is the depth of the reconstructed neuronal cell within a type-defining cortical layer; using at least the computed electric field potential to compute an activation function for axonal segments of the reconstructed neuronal cell; identifying a trigger area, wherein the trigger area comprises axonal segments of the reconstructed neuronal cell that possess activation function values above a threshold value; and computing the probability of reconstructed neuronal cell activation using at least a length of the trigger area.

In further embodiments, the method may comprise the additional steps of reorienting the reconstructed neuronal cell; repeating steps (a)-(e) for the reoriented reconstructed neuronal cell; and calculating an overall probability of activation, wherein the overall probability of activation is based on at least on the probability of the reconstructed neuronal cell activation and the probability of the reoriented reconstructed neuronal cell activation. In such embodiments, reorienting the reconstructed neuronal cell may comprise at least one of rotating the reconstructed neuronal cell or vertically shifting the reconstructed neuronal cell. In such embodiments, the vertical shifting of the reconstructed neuronal cell may occur within the range $[Z_{min}, Z_{min}+cL_s]$, where $Z_{min}$ is a minimal possible depth of the reconstructed neuronal cell soma, $L_s$ is a cortical layer size, and c is a coefficient.

In some embodiments, the threshold value compared to the activation function may be determined experimentally by matching a current-distance relationship that leads to a direct activation of the reconstructed neuronal cell from an electrical stimulation. In some embodiments, the activation function is represented by the equation:

$$f = \frac{d}{4\rho_i} \frac{\partial^2 \Phi}{\partial x^2},$$

where x represents the direction of an axonal fiber; $\Phi$ is a function representing extracellular potentials in the vicinity of axonal compartments; and $\rho_i$ represents a resistivity of axoplasm.

DETAILED DESCRIPTION OF THE EMBODIMENTS

Brain stimulation is increasingly common in basic medical and clinical research. Embodiments of the present disclosure include systems and methods for modeling and predicting the effect of cortical stimulation on spiking probability of neurons in a volume of tissue. This may be accomplished, for example, by combining an analytical estimate of stimulation-induced activation of different cell types across cortical layers, depending on the morphology and properties of their axonal arborization profiles. In various embodiments, methods can be adapted to different electrode configurations and stimulation protocols. As a result, methods can be implemented to predict the response activity of different cell types across cortical layers and to characterize the overall network dynamics following electrical stimulation on the cortical surface.

Embodiments of the systems and methods disclosed herein can be used to predict activation of different types of neuronal cells to extracellular electrical stimulation. This can be accomplished, for example, by defining the electrode configuration, and collecting morphological cell reconstructions. The defined electrode configuration may include parameters such as the depth of the surface electrode, the size and shape of the electrode, and the total current applied. In various embodiments, the method can be configured to compute the electric field potential in the brain tissue using the defined configuration for the stimulation. Then, using the potential, the method may compute effective transmembrane current along reconstructed cell arborization and define the probability of activation. Then, the method may use methods of statistical inference to predict average response in a given brain region for a given cell type.

FIG. 1 illustrates an example of an electric potential under an electrode plate and its effect of axonal fibers in accordance with various embodiments of the present disclosure. FIG. 1 shows a schematic representation of the example electrode in the X,Y,Z coordinate system, in which Z is the depth and X and Y are surface coordinates. In this example, the electrode is located on the surface, and the center of the coordinate system corresponds to the center of the electrode. In some embodiments, an electrode may be placed directly on a cortical surface and the electrode size and range of the currents used may be comparable to common experimental settings. For stimulation protocols that place the current source farther away from the cortical surface, the current may pass through other tissues, such as the skull, dura, arachnoid or pia maters before reaching the cortical layers. In such cases, embodiments may take into account potential capacitive properties, which effectively act as frequency filters, and current diffusion.

To estimate the effect an electrical stimulation has on the tissue, the electrical field potential of the current source may first be determined. The electrical field potential may be determined based on the size and shape of the electrode and the total current injected into the tissue. In some embodiments, the current may be assumed to be uniform across the electrode surface. Assume for example, an electrode implemented as a homogenous square electrode. In such an example, the resulting electric field potential $\Phi(X,Y,Z)$ may be calculated using the following expression:

$$\Phi(X, Y, Z) = \frac{1}{4\pi\sigma_e A^2} \int \int_{-A/2}^{A/2} \frac{dxdy}{\sqrt{(X-x)^2 + (Y-y)^2 + Z^2}} \quad (1)$$

where I denotes net current, $\sigma_e$ is the extracellular conductivity, and A is the edge length of the square electrode (e.g., as shown in FIG. 1). In other applications, the electrode surface may be of any size or shape and is not limited to a square geometry. Such other geometries may then be reflected in a modified equation (1).

Figure 2:
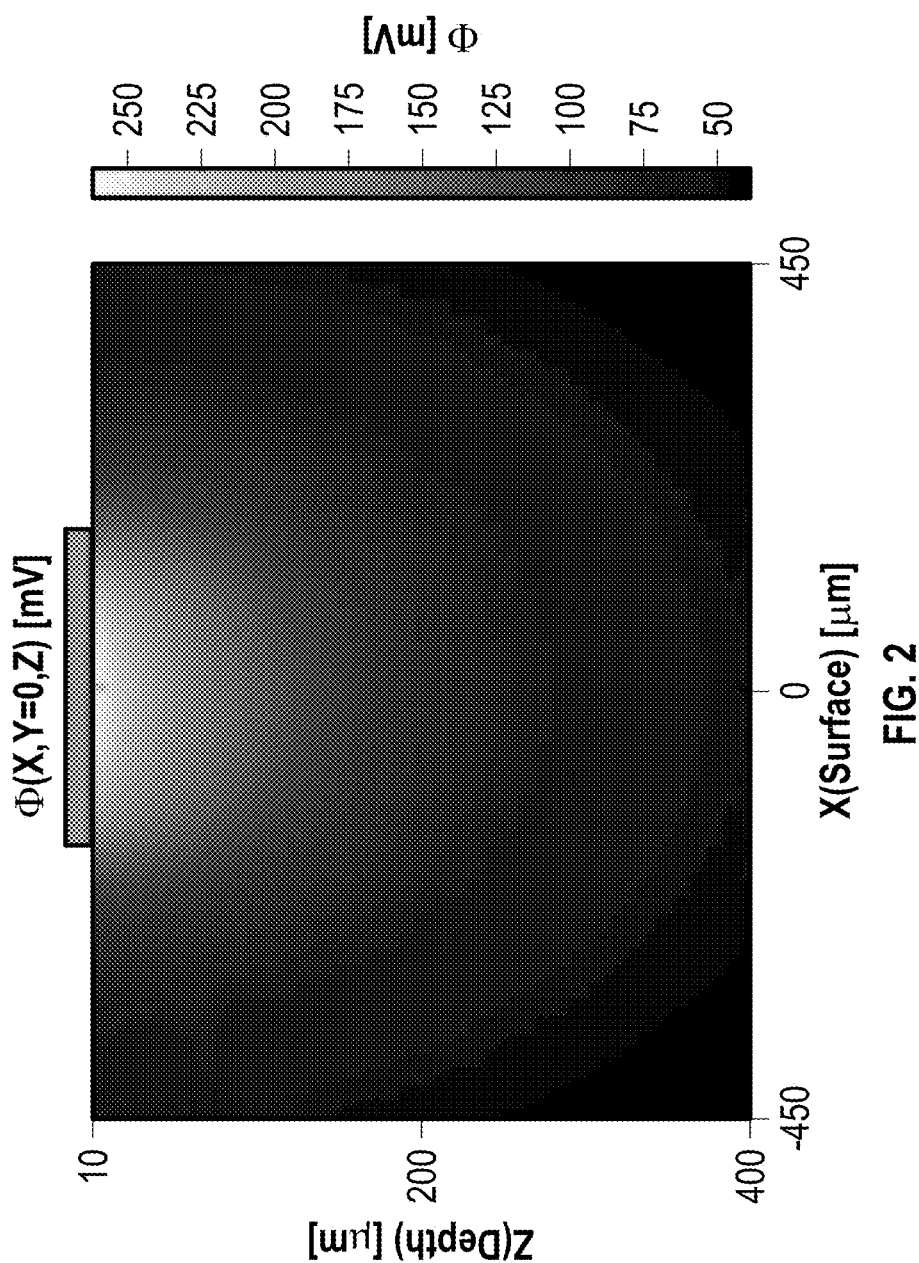
FIG. 2 is a graph that depicts an electric potential $\phi(X,Y,Z)$ on a the plane $Y=0$ in accordance with one embodiment of the present disclosure.

FIG. 2 depicts an electric field potential Φ(X,Y,Z) on the plane Y=0 in accordance with the above example. This example illustrates the rapid decay of potential with distance from the source electrode. For tissue locations farther away from the electrode plate, the point-source approximation may provide the following simplified expression to compute the electrical potential field:

$$\Phi(X, Y, Z) = \frac{1}{4\pi\sigma_e \sqrt{X^2 + Y^2 + Z^2}} \quad (2)$$

Equation (2) provides an approximation of the electric field potential at a distance from the electrode. However, Equation (2) is not useful for approximating electric field potential at locations right below the electrode plate, where the finite size of the electrode should be taken into account. This distinction is particularly relevant when considering the potential field of cortical layers I and II, which are immediately below the surface and are the most affected by stimulation due to the decay of Φ with depth. Therefore, close to the electrode, the point source approximation may not yield an estimate that can be used to predict the effect of cortical stimulation with sufficient precision.

The effect of applying a constant electric field to neuronal fibers can be described within one-dimensional cable theory, completed with the inclusion of the activation functions. According to this theory, the activation function ƒ(X,Y,Z) defines the effective transmembrane current that neuronal fibers (e.g. axons) receive due to extracellular electric stimulation. The activation function, ƒ, can be computed as the second order spatial derivative of the electric potential Φ along neuronal fibers. For the simplest case of a perfectly straight axon oriented horizontally in the Y=0 plane (e.g., FIG. 3), the activation function may have the following form:

$$f(X) = \frac{d}{4\rho_i} \frac{\partial^2 \Phi}{\partial x^2}, \quad (3)$$

where d is the diameter of the axon and $p_i$ is the resistivity of the axoplasm.

Figure 3:
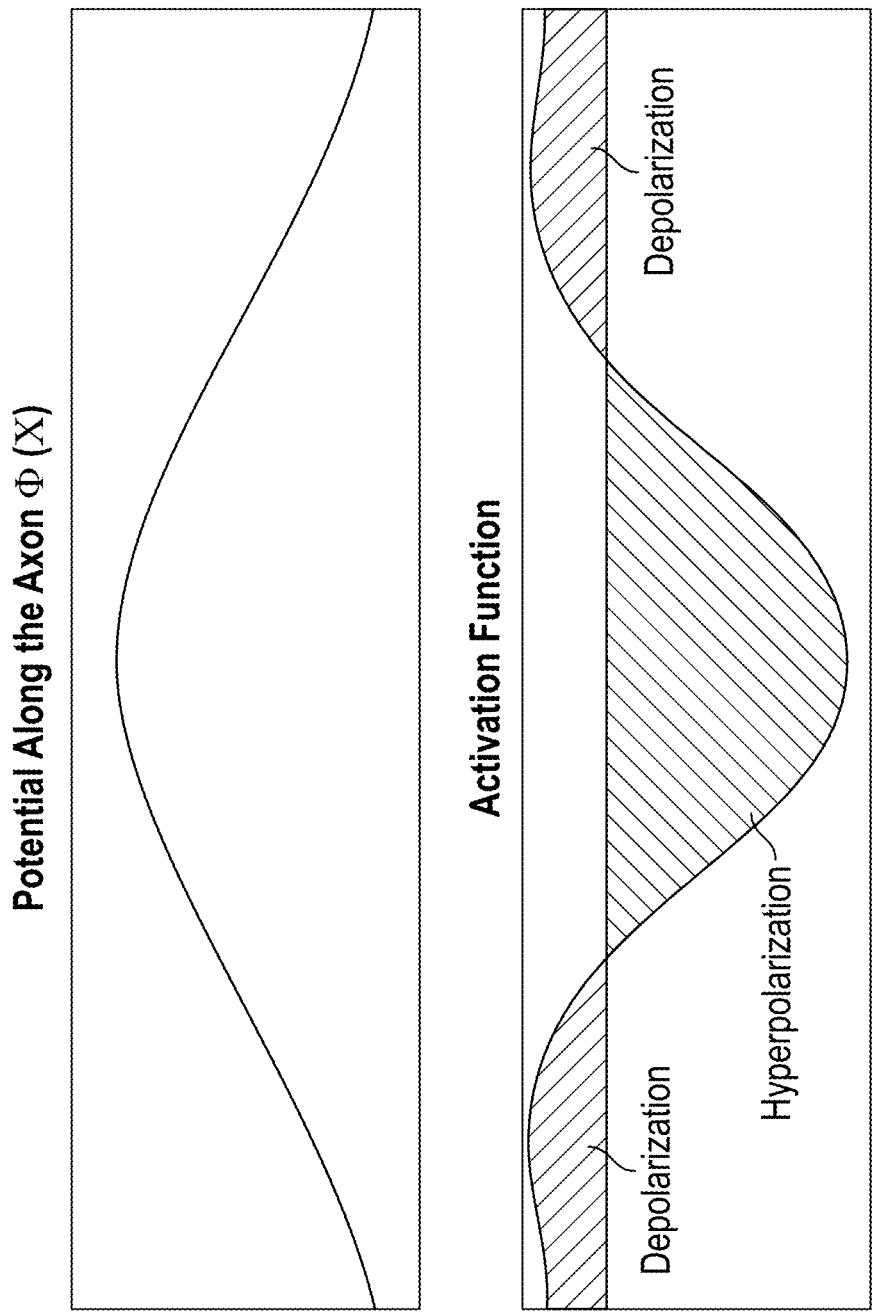
FIG. 3 illustrates the shape of the electrical potential $\phi(X)$ along the axon in accordance with various embodiments of the present disclosure.

As a result, the shape of the electrical potential Φ(X) along the axon, determines the function ƒ(X). An example of this is illustrated in the lower panel of FIG. 3, which shows the function ƒ(X). The activation function may useful for analyzing the effect of electrical stimulation on neuronal fibers because it provides putative activation and suppression zones along the fibers. In situations in which the horizontal axon receives anodal stimulation, the activation function along the axon shows that stimulation has a hyperpolarizing effect as shown in FIG. 3. The activation function along the axon also shows a slight depolarization effect in areas of the fiber further to the sides, as also indicated in FIG. 3.

Figure 4:
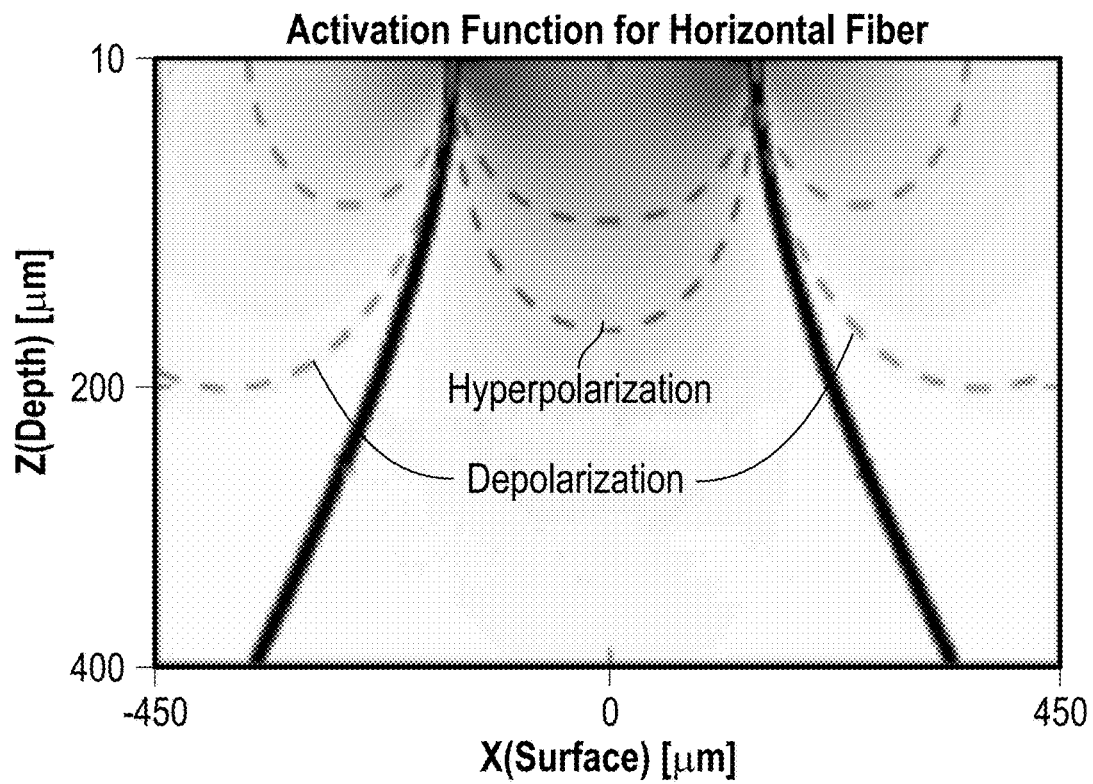
FIG. 4 depicts an activation function and polarization areas of a horizontally oriented fiber as a function of coordinates $X,Z$ on the plane $Y=0$ in accordance with various embodiments of the present disclosure.
Figure 5:
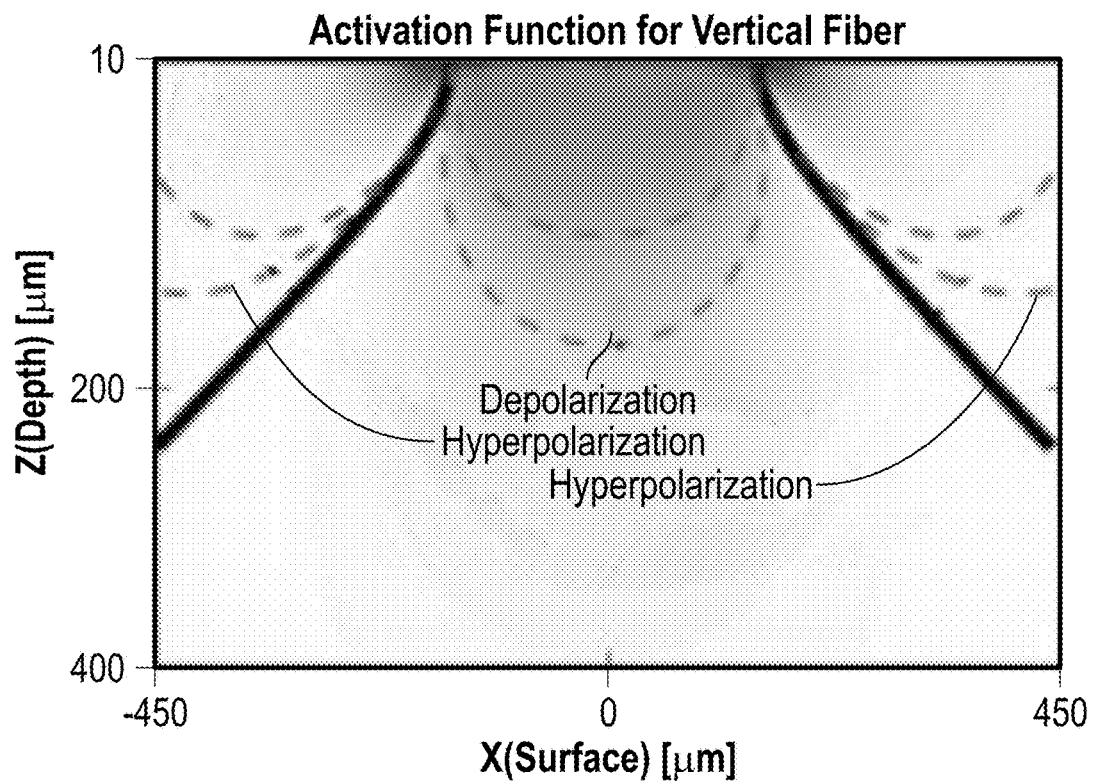
FIG. 5 depicts an activation function and polarization areas of a vertically oriented fiber as a function of coordinates $X,Z$ on the plane $Y=0$ in accordance with various embodiments of the present disclosure.

FIGS. 4 and 5 depict examples of the activation function for horizontally (FIG. 4) and vertically (FIG. 5) oriented fibers as a function of coordinates X,Z on the plane Y=0. The solid curves separate the areas of depolarization and hyperpolarization. FIG. 4 shows that the distance of the axonal fiber from the electrode influences the effect of the stimulation. In addition to the interplay of fiber orientation and placement, FIG. 5 also depicts the activation function ƒ(X, Y,Z) for vertically (ƒ) oriented axons. As these examples illustrate, the area below the electrode has a hyperpolarizing effect on horizontal fibers but a depolarizing effect on vertical ones. The spatial/orientation selectivity of the hyperpolarization/depolarization effect is still present when considering cathodal rather than anodal stimulation. However, with cathodal stimulation, the activation function would be reversed and the areas of depolarization and hyperpolarization would switch roles as compared to that shown in FIGS. 4-5.

The foregoing provides example embodiments for obtaining an analytical estimate of the electric potential and the activation function for neuronal fibers within cortical tissue. This disclosure now describes the impact such activation may have on specific populations of cortical neurons. The impact actually depends on several factors including, for example: (a) the effect of a current injected at a given distance from a neuron on the membrane voltage of that neuron; and (b) the distribution of different neuron types across layers. Indeed, different neuron types are distributed differently across cortical layers, and it is expected that their different properties and placement in the cortex would affect if and how these neurons respond to a surface electrical stimulation.

Electrical stimulation may directly drive a response in a cell. This can be accomplished, for example, by triggering an action potential in nodes of Ranvier, or by activating the axon initial segment (orthodromic spikes). Accordingly, embodiments may estimate the effects of stimulation on cells' axonal fibers, and ignore their dendritic arborizations. This analysis may determine how, on average, the axonal arbors of different cell types are laid out in the cortical tissue. Reconstructing a specific and complete 3D volume of cortical tissue with any precision is difficult if not impossible, and would introduce a strong limitation in the estimates due to its sensitivity to the specifics of the very tissue reconstructed. However, because multiple databases containing the detailed reconstructions of different cell types from different preparations are available, embodiments may implement a new method to build an approximation of a volume distribution of its axonal arborization for each cell type. This can be done in some embodiments by using the large datasets available on the specific anatomy of different cortical cell types. Indeed, the neuronal response to stimulation can be predicted using reconstructed anatomy to define average arborization profiles.

Figure 6A:
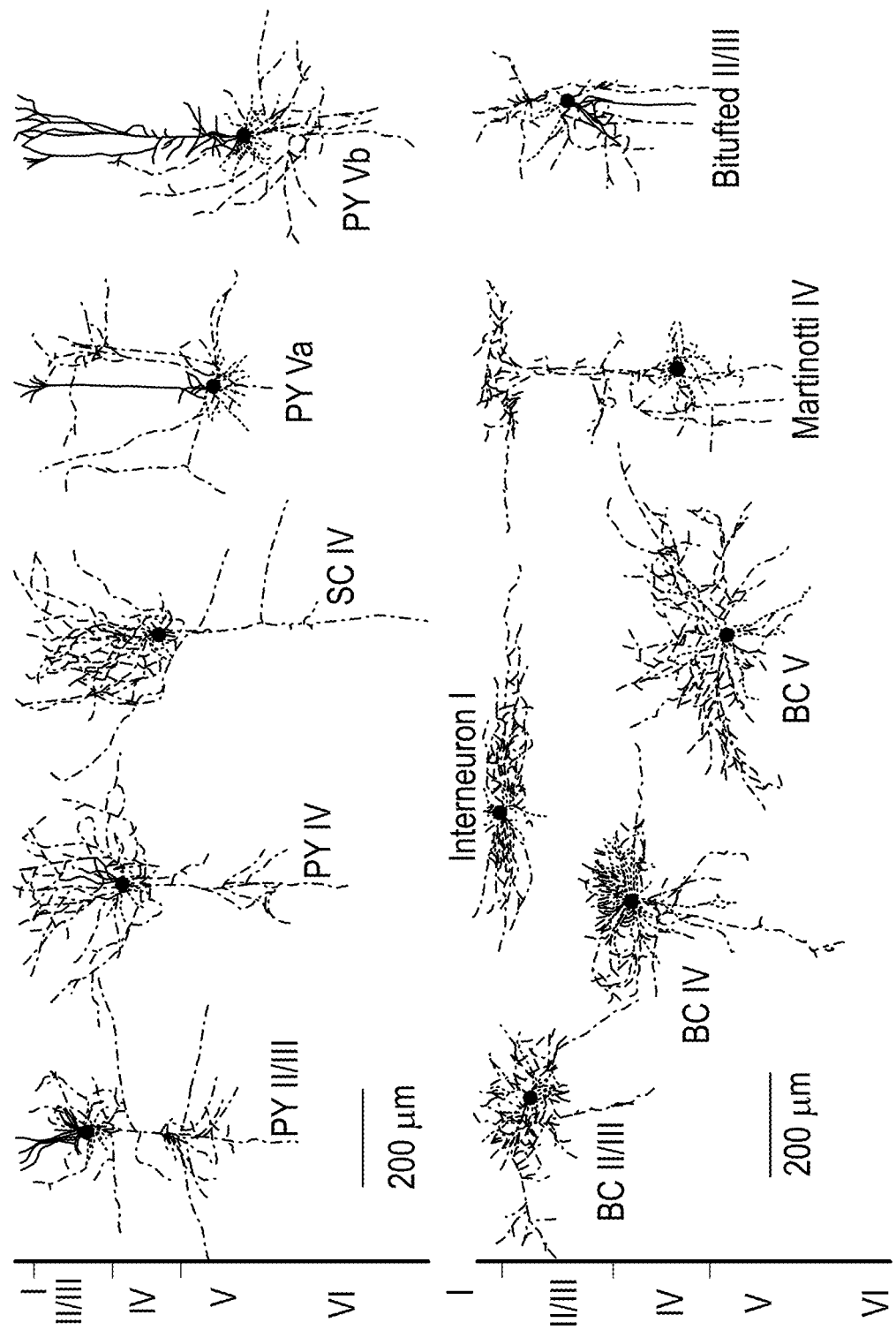
FIG. 6A depicts the average axonal densities formed by neurons of each specific type in accordance with various embodiments of the present disclosure.

In some embodiments, the average profile of the probability that a cell axonal arborization would occupy a given volume across layers can be determined. FIG. 6A depicts typical anatomical profiles for the main types of cortical neurons: axon, apical dendrite, and the basal dendrite. The dot shows the soma position. The top row exhibits excitatory cells (PY—pyramidal neurons, SC—spiny stellate cell). The bottom row contains inhibitory interneurons (BC—basket cell).

This example shows reconstructions for the different cell types that may be considered: pyramidal cells (PYs), excitatory spiny stellate cells (SCs) from layer IV, basket cells (BCs), Martinotti cells (MCs) and bi-tufted interneurons. There are two types of PYs in layer V: slender-tufted neurons from layer Va and thick-tufted cells from layer Vb. In this example, BCs include three subtypes according to the classification proposed in recent experimental works: large, nest and small basket cells. According to the canonical cortical microcircuit model, PYs and SCs from layers IV and Va receive input from thalamus and then innervate superficial layers, providing an incoming flow of information into cortical column. In turn, thick-tufted PYs (Vb) integrate the overall activity within and across columns, both neighboring and distant, and project their output to subcortical regions.

Interneurons in the cortex are very diverse in their morphology and functionality. BCs constitute about 50% of all inhibitory cells in the cortex and form the primary source of lateral inhibition within layers, targeting somas and/or proximal dendrites of PYs. MCs comprise another significant fraction of interneurons, which can form cross-layer as well as cross-columnar inhibitory connections. These cells have a specific structure, with dense axonal arborization in layer I where they inhibit tuft and proximal dendrites of PYs from all layers. MCs are numerous especially in infragranular layers, where they are also known to specifically target basal dendrites of excitatory neurons from layer IV. In the cortex, there are several other classes of interneurons which are found in fewer numbers: layer I interneurons, bipolar, double bouquet and bi-tufted cells. The analysis described herein includes bi-tufted and layer I interneurons, as representative examples of this dendrite-targeting class of interneurons. This population of reconstructed layer I interneurons contains 3 distinct subclasses (classification from Muralidhar et. al.): small, horizontal and descending interneurons.

Figure 6B:
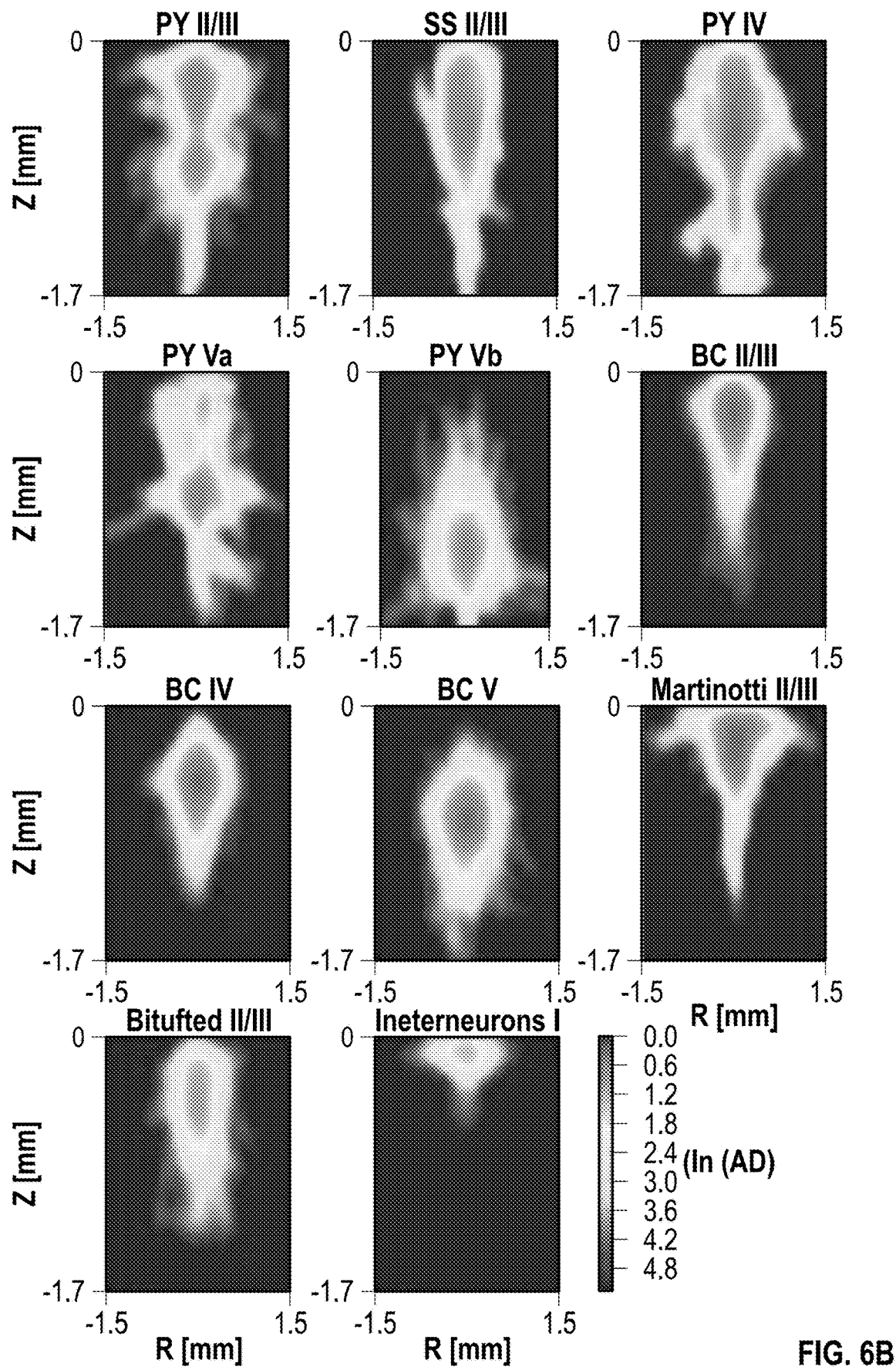
FIG. 6B depicts the average axonal densities in logarithmic scale formed by neurons of each specific type in accordance with various embodiments of the present disclosure.

Multiple single-cell reconstructions for the same cell type can be used in some embodiments to determine an average profile of the probability that a cell axonal arborization would occupy a given volume across layers. Examples of the average axonal densities are shown in FIG. 6B in logarithmic scale to emphasize the details of the differences across shapes. This shows an example of the average axonal densities formed by neurons of each specific type (e.g., pyramidal neurons, spiny stellate cell, and basket cell). The shading denotes the logarithm of averaged axonal density (AD), computed over a set of available reconstructions of cortical cells. The logarithmic scale is used for better visualization of axonal arborization. This provides a general intuition on the generic shape of the axonal arborization for distinct types of cortical cells.

Averaged axonal density represents overall morphological properties of a given type of neuron and can provide a general intuition on how a given cell type can be affected by electrical stimulation. In various embodiments, the axonal density may be computed as follows: first, all 3D reconstructions of cells of a certain type are aligned in space and centered at the soma, such that axis coordinates (x, y, z) correspond to width, height and depth of the slice respectively. Second, all reconstructions can be superimposed in a 3D volume, and the axonal density constructed on a grid of a size 100 points in the x direction, by 100 points in the y direction, by 50 points in the z direction. Finally, the 3D density array can be averaged across the z-axis and the result plotted. The example of FIG. 6B is plotted in a logarithmic scale.

All types of excitatory cells, except thick-tufted PYs from layer Vb, have relatively dense axonal arborization in the top layer, which is reached by the strongest current density during surface-placed electrode stimulation (e.g., such as that shown in FIG. 1). As for the interneurons, BCs axonal arborizations are largely contained within the layer occupied by their soma, while Martinotti and bi-tufted cells show axons with a wider vertical span and a large footprint in the top layer (FIG. 6B). The axonal density of layer I cells is mainly confined in the top layer with small traces towards layer II, due to so-called descending interneurons.

Thus, a collection of reconstructed cortical cells may be combined to create an average profile of the axonal arborizations. By way of example, to integrate the anatomical data and the estimated activation functions, the activation function capable of triggering a response in the neuron may be identified. To compute such a threshold, the current-distance relationship leading to direct activation of a cortical cell by the depth electrode may be matched. By way of example, the experimental data may be matched to define a value of the threshold injected current, which may be applied to induce a threshold effective current at the initial segment located at a select distance from the electrode.

The average axonal arborization and activation function as determined can provide an estimate for the probability of the axonal spiking response. The foregoing describes embodiments for (i) determining the electric potential in the tissue under the stimulating electrode and computing the activation function for axons, and (ii) using a collection of the reconstructed cortical cells, together with the average profile of their axonal arborizations, to predict a neuronal response to stimulation. In various embodiments, the anatomical data and the estimated activation functions may be integrated by identifying when the activation function is capable of triggering a response in the neuron. To compute such threshold, some embodiments can be implemented to match the experimentally measured current-distance relationship leading to direct activation of cortical cells by the depth electrode.

Figure 7A:
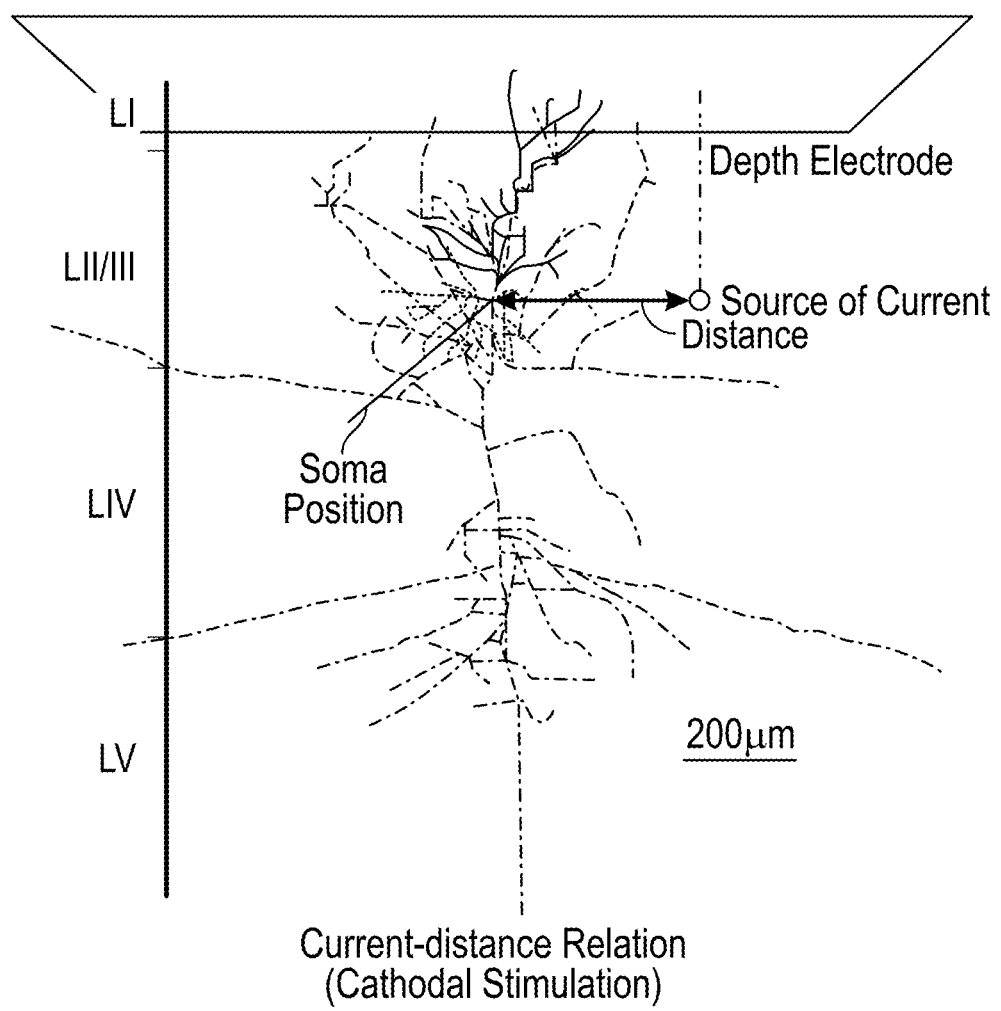
FIG. 7A illustrates a direct activation of a cell by a depth electrode in accordance with various embodiments of the present disclosure.
Figure 7B:
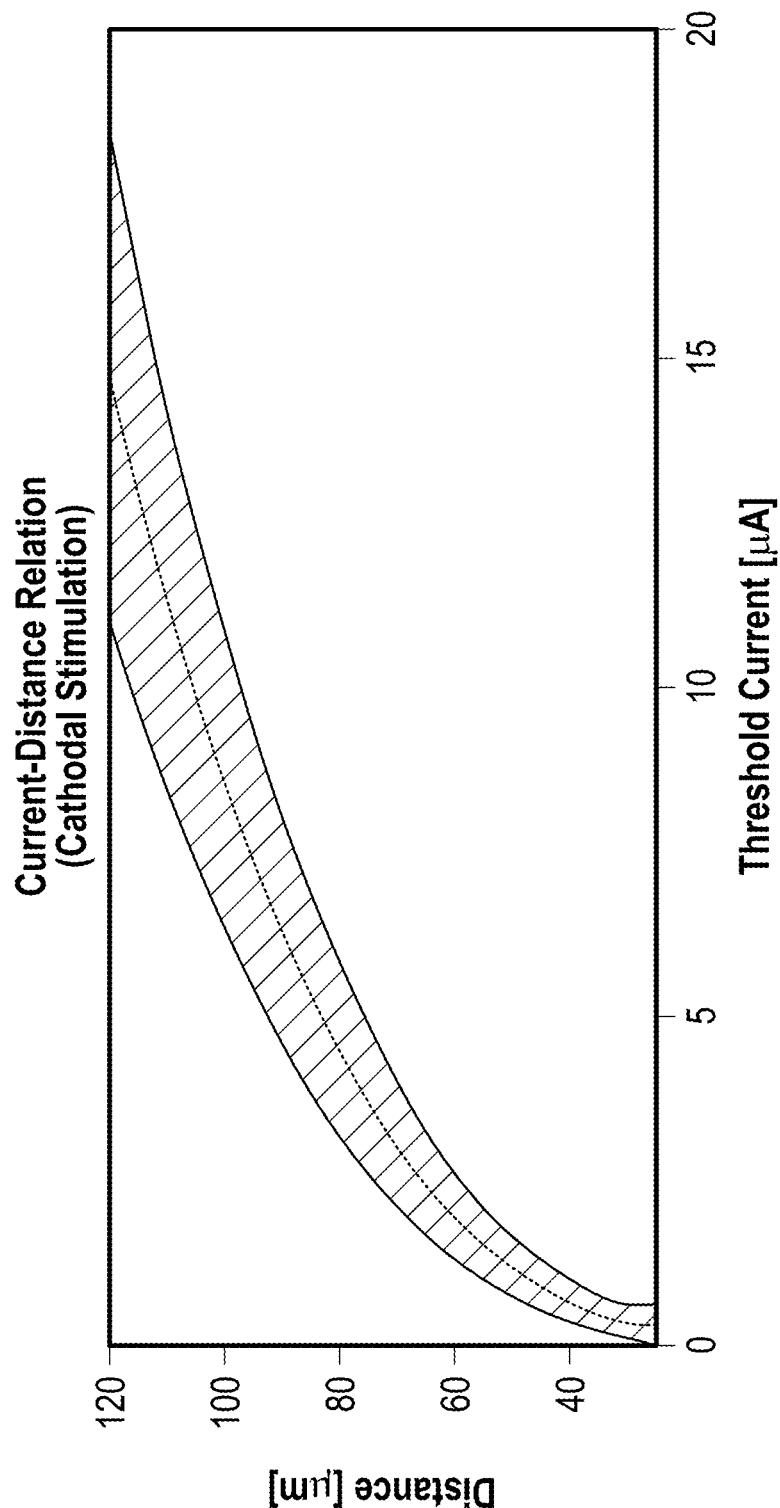
FIG. 7B shows a current-distance relation for a direct activation of pyramidal cells by a depth electrode in accordance with various embodiments of the present disclosure.

FIG. 7A illustrates an example of direct activation of a cell by a depth electrode in accordance with various embodiments of the present disclosure. FIG. 7A is a schematic representation of a depth electrode (point source of current) and a pyramidal cell. FIG. 7B shows a current-distance relation for direct activation of pyramidal cells (initial segment) by the depth electrode. The internal line represents an average dependence across array of pyramidal cells, while the grey area denotes the mean plus/minus standard deviation. An ensemble of 15 cells was used for this example.

In the example of FIG. 7A, showing an in vivo experiment, the depth electrode (modeled as a point source of current) was placed near a cell body of a reconstructed pyramidal neuron from layer II/III. Equations (2) and (3) can be used to compute the activation current $f$ at the axon initial segment (because the experimental data was focused on orthodromic activation), for different values of stimulation current/and distances d. This revealed that for fixed values $f$=Const, the resulting relation I(d) had a characteristic quadratic form, which qualitatively resembled experimental dependencies of the threshold activation current on distance. By determining $f$=$f$th–3 pA/um$^2$, the current-distance relationship may be obtained. Thus, when the electrode is placed at a depth close to the soma, a threshold value $f$th for the cathodal current may be determined while the anodal current does not induce any depolarizing effect on the axonal initial segment.

Figure 8:
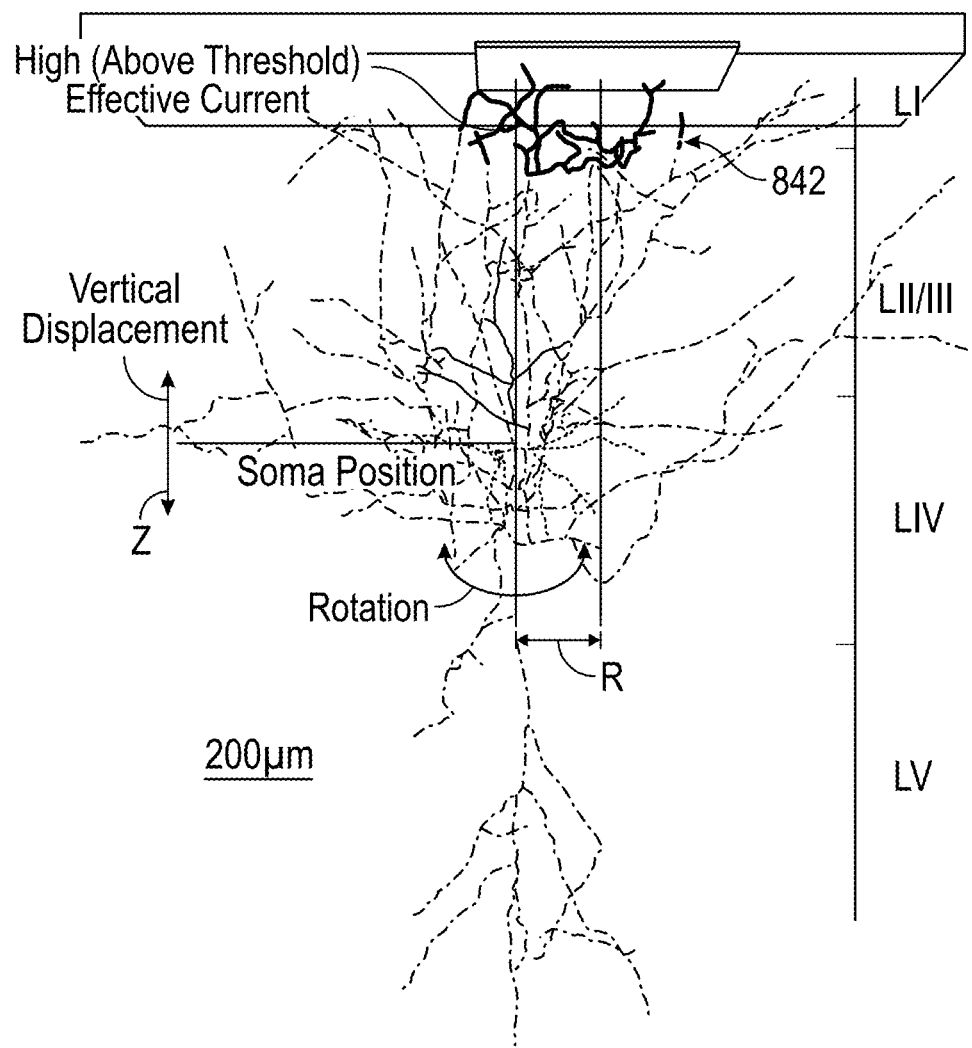
FIG. 8 depicts an estimation of the activation probability induced by surface stimulation in accordance with various embodiments of the present disclosure.

In some embodiments, a threshold value for each axonal segment can be estimated. Once the threshold value for each axonal segment is estimated, the overall effect of stimulation on a cell may be determined by taking into account the entire axonal arbor. FIG. 8 illustrates an example of an estimation of the activation probability induced by surface stimulation. More particularly, this shows an example of typical layer IV pyramidal cell. For each cell, R and Z (depth) parameters are assigned. The activation function identifies its trigger area 842, where the effective current is above the threshold value. Action potentials can be initiated in these segments and propagate along the axonal arborization. To populate a statistical set (to find the average probability of spiking), each cell reconstruction may be shuffled by rotating and shifting along the vertical axis (indicated by bold arrows), and multiple reconstructions may be considered for each cell type (e.g., up to a total of 561 cells).

In some embodiments, the probability of cell activation can be estimated by first computing the activation function $f$ along the entire axon arbor, and by comparing $f$ to the threshold value $f$th, the axonal segments that are potentially activated can be identified. An example of potentially activated axonal segments is shown in FIG. 8 at 842. Together these segments form a total "trigger" area of length L. Thus, for the trigger area to initiate axonal activation in the case of myelinated axons, it should contain at least one node of Ranvier where the current exceeds the threshold value $f$th. Therefore, the overall probability of cell activation depends on the length of the trigger area L and the probability of occurrence of nodes of Ranvier, which can be found using the average internodal distance. Therefore, a larger length of trigger area L or a smaller internodal distance along the axon, or both, lead to a higher activation probability. In the case of unmyelinated fibers, the entire membrane of axon is exposed to the extracellular space and, therefore, the cell activation probability depends only on the length L. For cell types with unmyelinated axons a binary dependence can be used such that the presence of a trigger area (i.e., L>0) produces activation, while the absence of a trigger area (i.e., L=0) means no activation. However, because unmyelinated axons are less excitable, their threshold of activation ($f$th) is much higher compared to nodes of Ranvier and axonal hillock. In some embodiments, a threshold of 20-fold larger can be used. In summary, the length L of the trigger area can be computed using the activation function, and then transformed into probability of spiking for a given cell.

To account for natural variability in cortical cell types and their locations with respect to the current source, some embodiments can use the approach represented in FIG. 8. For each anatomical reconstruction of a given cell type, embodiments can be implemented to assign a position R, which marks its planar distance from the center of the electrode plate, and a coordinate Z (depth), which locates its soma within the appropriate cortical layer. The process can then identify (based on the length of trigger area L) the probability of axonal activation for a given cell configuration within the cortical volume. Additionally, the cell can be rotated and its soma shifted in the vertical direction (e.g., for a range of Z values that still keep the cell within its type-defining layer, see FIG. 8). This yields numerous data samples for a given neuron reconstruction placed at a distance R, and each may be evaluated if the neuron would be activated. The probability of activation for a given cell reconstruction (across all available rotations and vertical shifts) may be given by the fraction of samples that were activated over the total number of samples. This procedure can be repeated for each reconstructed cell belonging to a given cell type, obtaining a probability of activation for each of them. The average of all these probabilities can be computed to determine a faithful estimate of the probability of activation for a cell of a given type placed at distance R from the electrode.

Figure 9:
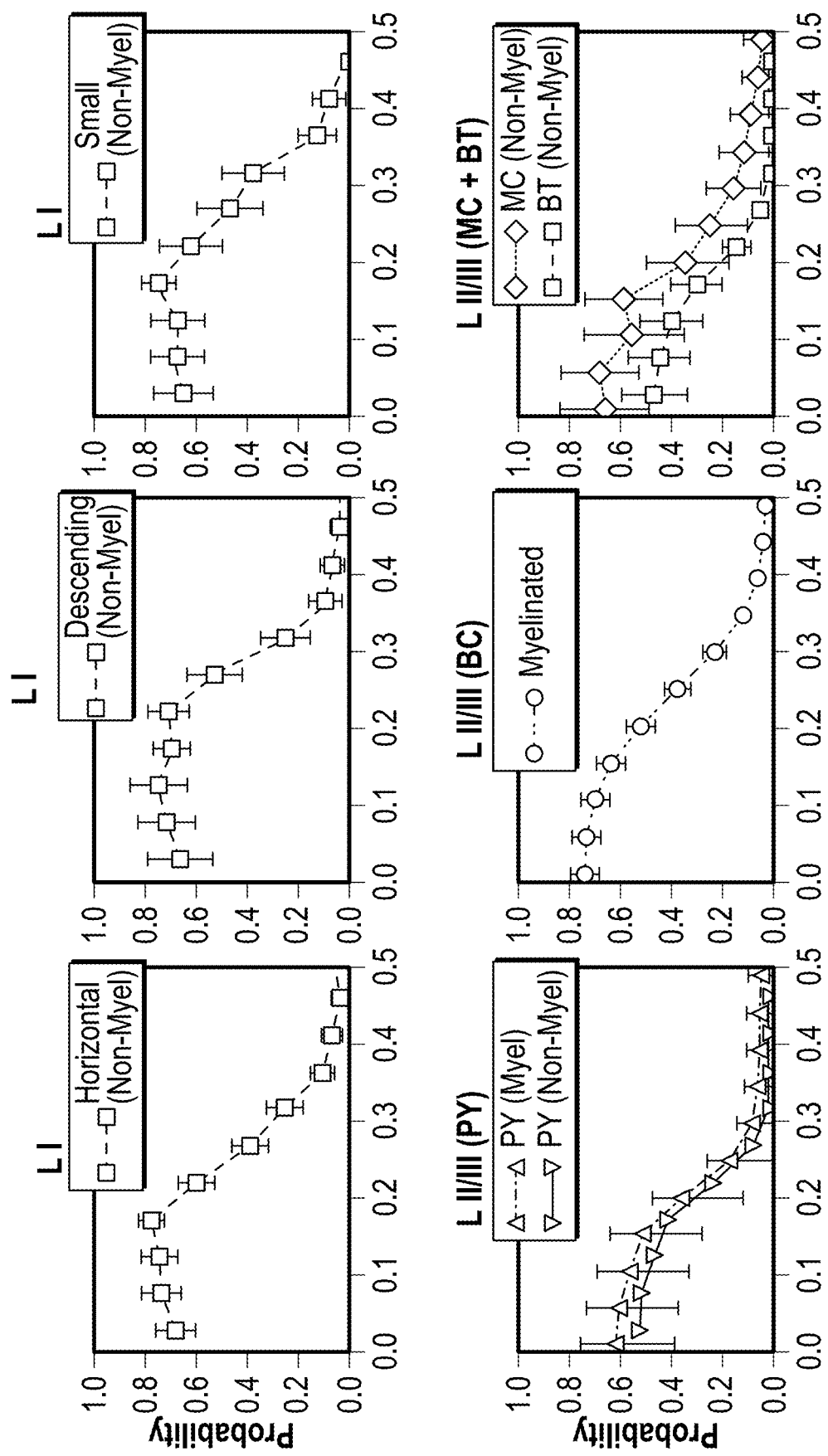
FIG. 9 illustrates examples of stimulation applied by a superficial cortical electrode in accordance with various embodiments of the present disclosure.
Figure 9:
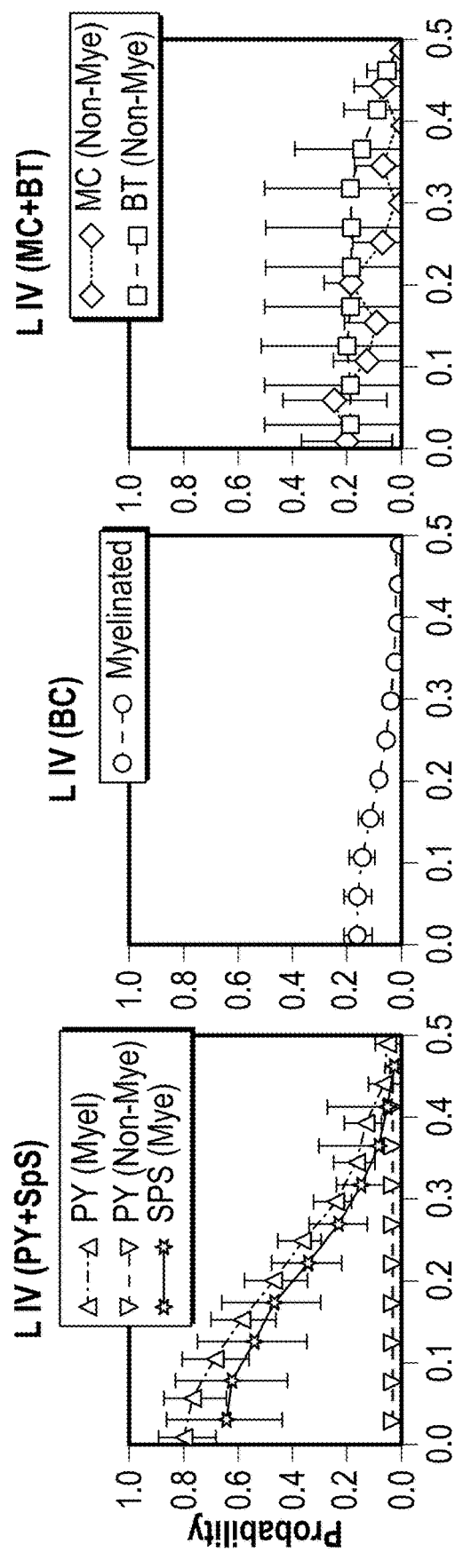
Figure 9:
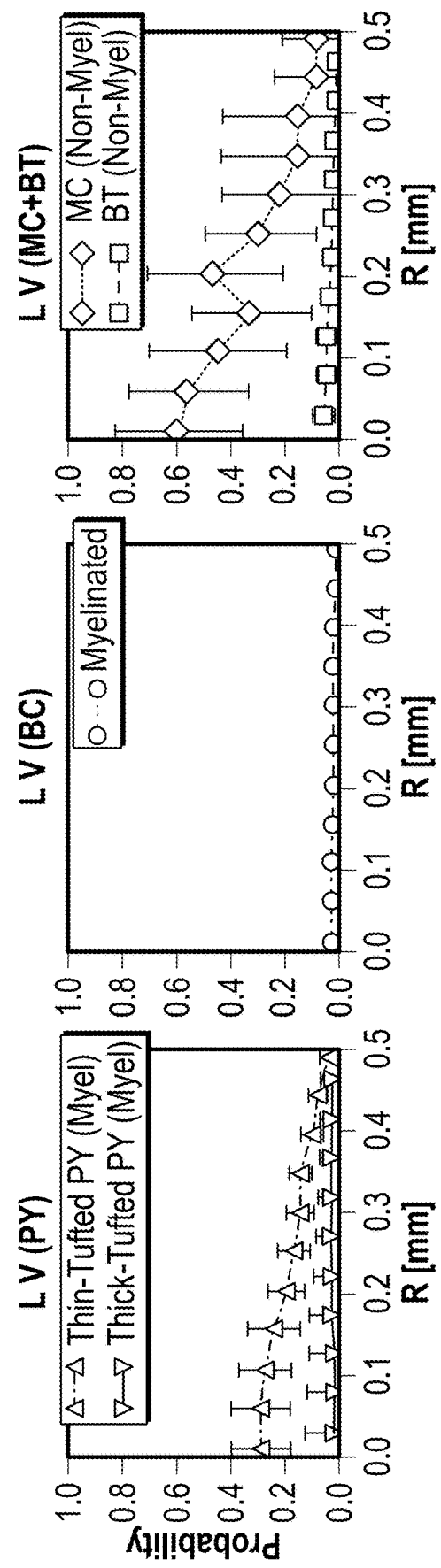

It should be noted that distinct cell types show different profiles of activation probability. Embodiments may be implemented to define an activation probability function, depending on the planar distance between a cell soma and the electrode (R in FIG. 8), which can be different for different cell types. FIG. 9 illustrates an example of the disclosed method applied to stimulation by a superficial cortical electrode. Because the initial analysis suggests that anodal stimulation is most effective at depolarizing vertically oriented axonal arbors (see FIGS. 4-5), this illustrates example analysis for the case of anodal stimulation. Referring still to FIG. 9, the top row shows a direct activation probability for 3 distinct types of layer I interneurons. Rows 2-4 (when viewed from top to bottom) correspond to layers II-V. The left column contains the probability for excitatory cells (pyramidal and spiny stellate), the middle column contains data on soma/proximal dendrite-targeting interneurons (basket cells) and the right column contains the probability for tuft/proximal dendrite-targeting interneurons (Martinotti and bitufted cells). The data represent anodal stimulation (I=275 µA). This disclosure describes the results of this example analysis for different cell types and the role of myelination in activation probability.

The left column of FIG. 9, rows 2-4 leads to the prediction that pyramidal cells in most cortical layers would be only moderately activated by the superficial stimulation, with the exception of excitatory cells (PYs and SCs) in layer IV, which have a fairly high probability to spike (80% right below the electrode) in response to the current stimulation. Layer IV excitatory cells receive input from the thalamus and other subcortical structures, and locally amplify such input (by strong recurrent connectivity) before projecting it to layer II/III pyramidal cells. Accordingly, their higher probability of activation in response to input suggests a possibility for superficial stimulation to be able to compensate for lacking subcortical inputs (for example following injury).

Within layer V, slender-tufted PYs (Va) have a moderate chance of direct activation (FIG. 9, bottom row, left), compared to thick-tufted PYs, which do not seem to be directly recruited by the surface stimulation (FIG. 9, bottom row, left). This difference is consistent with their average axonal arborizations (FIG. 6B): slender-tufted PYs tend to project their axons to the superficial layers, while thick-tufted PYs axonal density is sitting away from the superficial layers. Because thick-tufted PYs are the main output of a cortical column, their activation effectively controls whether external electrical stimulation can influence downstream signaling to other brain regions. Therefore, to activate the cortical output, external stimulation should first trigger enough of a local circuit response so that the thick-tufted pyramidal cells in layer V can be recruited by the evoked neuronal activity of other cell types.

The central column of FIG. 9 (rows 2-4) shows that activation of BCs is very layer-specific; in particular, layer II/III BCs are easily activated, while deeper layer BCs are much less likely to be recruited. This estimate accounts for myelination in their axonal fibers (discussed in detail below), and is consistent with the localized organization of BCs' average axonal densities (FIG. 6B). Because BCs are the primary source of inhibition within each layer (they are the largest fraction of interneuron found in any cortical column), their activation profile has the potential to shape the spiking within the cortical network. The fact that layer IV BCs are not directly recruited by input current further enables layer IV excitatory cells to trigger activity in the cortical column.

The rightmost column and top row of FIG. 9 illustrate the likelihood of activation for other non-parvalbumin interneuron types, which have unmyelinated axons and are likely to contact pyramidal cells in their distal dendrites. It is important to note that MCs from the infragranular layers (IV-VI) also target basal dendrites of the excitatory cells in layer IV.

MCs have a high activation probability in layers II/III and V, which is consistent with their specific axonal density distribution (FIG. 6B). Extensive axonal arborization in layer I led to a high activation probability even though their axons are unmyelinated. Note that layer IV MCs show less activation than MCs in other layers, driven by the atypical shape of the axonal arbors in the reconstructions available.

Bitufted cells have moderate probability of activation only in supragranular layers. Expectedly, layer I interneurons being the closest to the current source, also exhibit high activation probability (FIG. 9, top row). This leads to a prediction that a surface stimulation would recruit a fair amount of spiking in cells that are responsible for diffused and cross-layer inhibitory signaling, within and across cortical columns. It may further suggest that cortical stimulation by the surface electrode, while capable of triggering spikes in excitatory cells in deep layers, is not likely to evoke very strong excitatory events in the underlying tissue.

The presence of myelin along an axonal fiber is considered an indication of high excitability. This is because the nodes of Ranvier in between myelinated segments are known to contain a high density of sodium channels. Therefore, when estimating the probability of activation due to stimulation, the effect of myelin may be included by assuming a significantly higher activation threshold for unmyelinated fibers, compared to segments with nodes of Ranvier and axonal initial segments.

Furthermore, a non-uniform distribution of myelin can affect overall response to stimulation. Layer II/III pyramidal neurons exhibit complex intermittent myelination patterns, where myelinated segments alternate with long unmyelinated paths. The leftmost column in FIG. 9 compares activation probabilities for myelinated and unmyelinated pyramidal neurons. Layer II/III PYs showed no significant difference in activation probabilities due to myelination. In contrast, PYs from layer IV showed a drastic difference: with 80% activation in the presence of myelin and almost null activation probability for unmyelinated fibers.

Accordingly, in general, the above-described experiments show that cells with somas (and axonal initial segment) close enough to the superficial stimulation electrode and vertically oriented axonal arbors (like PYs in layer II/III) are not likely to see a great loss of activation probability if they lack myelination. In fact, the above-described experiments show that myelination plays a strong role in promoting cell excitability for cells that have axonal initial segments in deeper layers, farther away from the current source (like PYs in layer IV). This is because they would rely more strongly on action potential in distal axonal fibers in the superficial layers to be generated by the input. The principle that unmyelinated fibers can be activated despite their lower excitability as long as they are placed closed enough to the current source applies also to interneurons. In fact, Bitufted cells and Layer I interneurons (which are unmyelinated) show moderate activation probabilities in supragranular layers but no activation for deeper layers. Martinotti cells, although unmyelinated, do not show strong difference in their activation probability across cell layers. This is due to their specific shape, characterized by extensive axonal arborization in the upper layers.

As these embodiments illustrate, the probability of cell activation depends directly on the fraction of axonal arborization which has an activation function above threshold (length of the trigger area). In turn, this length depends on the amount of overall stimulation current, I, delivered by the electrode. Intuitively, the larger the current magnitude, the longer the trigger area (FIG. 8), and hence the higher the spiking probability. However, it is less clear how changing the stimulation polarity would affect the likelihood of cell activation (FIG. 8), since different types of stimulation have completely different effect on axonal fibers: below the electrode, anodal current depolarizes vertical fibers and hyperpolarizes horizontal fibers, while cathodal current has the opposite effect (FIGS. 4,5). Therefore, embodiments can determine to what extent the probabilities of cell activation (FIG. 9) depend on the amplitude and polarity of the stimulating current I, and whether this dependence is similar across different cell types with different anatomies (FIG. 6B). Accordingly, embodiments of the methods disclosed herein can be applied to estimate the activation probability (FIG. 9) when the electrode delivers different amounts of total current I. This probability may be estimated in a volume nearby the stimulating electrode, and each estimate repeated for the case of anodal and cathodal stimulation separately.

Figures 10A, 10B, 10C:
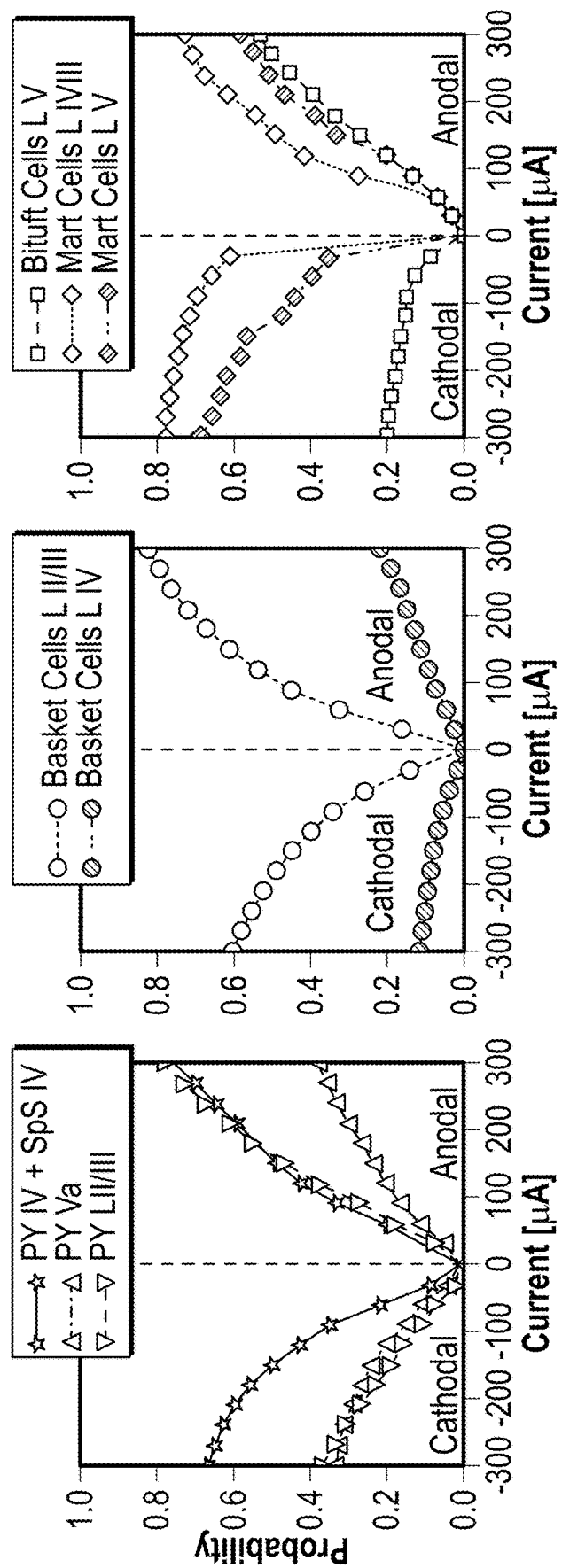
FIG. 10A illustrates the probability of activation for different Pyramidal and Spiny Stellate cell types undergoing different stimulation types (anodal or cathodal) in accordance with one embodiment of the present disclosure.
FIG. 10B illustrates the probability of activation for different Basket cell types undergoing different stimulation types (anodal or cathodal) in accordance with one embodiment of the present disclosure.
FIG. 10C illustrates the probability of activation for different Bituft and Martinotti cell types undergoing different stimulation types (anodal or cathodal) in accordance with one embodiment of the present disclosure.
Figure 10D:
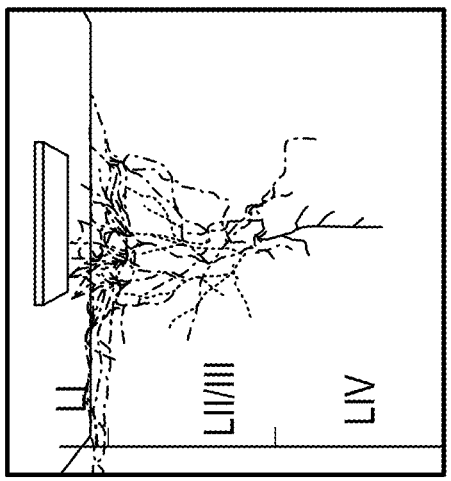
FIG. 10D illustrates an example activation for PY LII/LIII cells undergoing anodal stimulation.
Figure 10E:
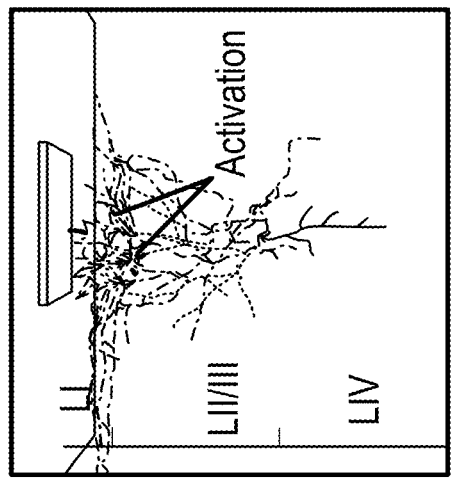
FIG. 10E illustrates an example activation for PY LIV cells undergoing anodal stimulation.
Figure 10F:
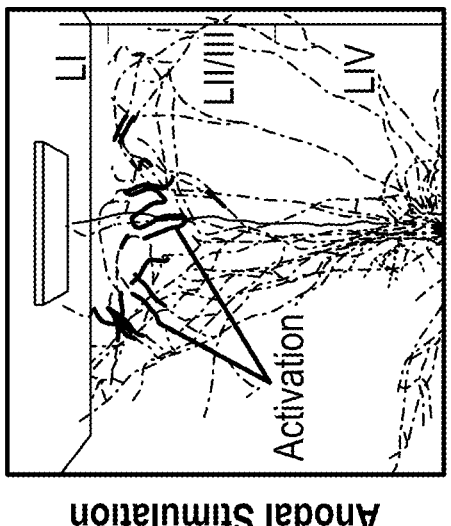
FIG. 10F illustrates an example activation for Martinotti LI/LIII cells undergoing anodal stimulation.
Figure 10G:
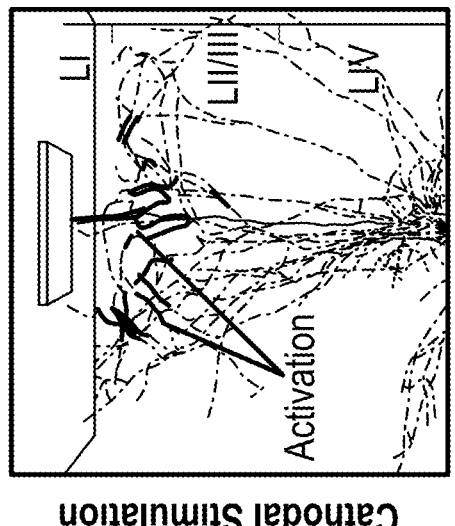
FIG. 10G illustrates an example activation for PY LII/LIII cells undergoing cathodal stimulation.
Figure 10H:
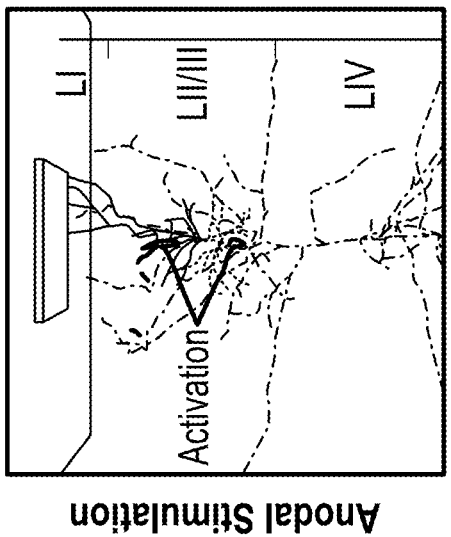
FIG. 10H illustrates an example activation for PY LII/LIII cells undergoing cathodal stimulation.
Figure 10I:
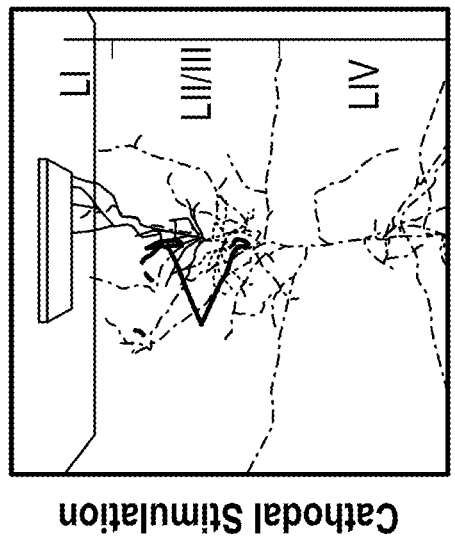
FIG. 10I illustrates an example activation for Martinotti LI/LIII cells undergoing cathodal stimulation.

FIG. 10A, FIG. 10B, and FIG. 10C each show how the overall activation probability changes as a function of the net current of stimulation (the total current used for the example of FIG. 9 was 275 μA) for different cell types. This shows that different cell types have distinct preferences for a stimulation type (anodal or cathodal). FIG. 10A, FIG. 10B, and FIG. 10C show the dependence of the activation probability on the net electrode current I for excitatory cells (FIG. 10A), basket cells (FIG. 10B), Martinotti and bi-tufted cells (FIG. 10C). FIG. 10D and FIG. 10G show that anodal stimulation (FIG. 10D) activates pyramidal cells LII/III more effectively than cathodal stimulation (FIG. 10G). FIG. 10E and FIG. 10H show that pyramidal LIV/V and spiny stellate cells have no preference for any type of stimulation. Because of the rich axonal arborization in supragranular layers, both types of stimulation can provide a large activation area. FIG. 10F and FIG. 10I show that cathodal current is more effective in activation of non-myelinated horizontal axons of Martinotti cells in supragranular layers.

All cells can typically be divided into three main categories based on their response types to the current: cells that respond more strongly to anodal stimulation, cells with a mild preference for responding to anodal stimulation, and cells that respond more strongly to cathodal stimulation. In fact, a cell position across cortical layers and the shape of its axonal arborization defines its preference to stimulation type. Each of these are now described.

Pyramidal neurons from layer II/III constitute a first class of cells, which is characterized by strong preference for anodal stimulation. The probability dependence on the current can be very asymmetric for this class of cells (FIG. 1) due to much higher probabilities for positive I>0 current (anodal stimulation). FIG. 10D and FIG. 10G show examples of the trigger areas (Activation) for a pyramidal cell from LII/III exposed to anodal vs cathodal stimulation. As can be seen in FIG. 10D anodal stimulation activated several vertically oriented branches close to the soma. In fact, in general anodal stimulation depolarizes vertical fibers (FIGS. 4-5). In contrast, the same magnitude of cathodal stimulation was not able to produce any trigger area in this example FIG. 10G because cathodal stimulation is not effective at depolarizing vertical fibers.

The second class of cells includes cells with a weak preference for a notable stimulation. These cells showed a slightly asymmetric relation between probability and current (FIG. 10A and FIG. 10B) and did not show any significant preference for a type of stimulation. This group exhibited spiny stellate cells, PYs from layer IV, slender-tufted PYs from layer V and basket cells from LII/III. As a representative example of this case, we show in FIG. 10E and FIG. 10H the trigger area of a LIV PY cell exposed to anodal vs cathodal stimulation. This cell has an extensive axonal arborization in layers I and II, containing a large number of variously oriented fibers. This arborization with no dominant directions results in a response profile that cannot differentiate between anodal and cathodal current input, because the lengths of the trigger area created by the different types of stimulation are similar (even if specific fibers which cross the threshold are different). This is evident in FIG. 10E and FIG. 10H, where the Activation areas (trigger area) are different in the two panels, but cover a similar amount of the axonal arbor. Similar arborization profiles, with no specific dominant orientation among the axonal fibers, are typical of all cell types included in this category (FIG. 6A), and therefore result in a similar lack of selectivity of these cells for anodal or cathodal stimulation.

Martinotti cells are the one cell type in this group that shows a strong preference for cathodal stimulation at relatively small magnitudes ($|I| \lesssim 150$ µA) (FIG. 10C). However, when the stimulation current is strong, they respond to either stimulation type. The strong response at low magnitudes for cathodal current in MCs is driven by their peculiar arborization. These cells are characterized by a large number of horizontally oriented fibers in layer I (FIG. 6B, FIG. 10F and FIG. 10I), which are likely to get activated in the presence of cathodal stimulation (FIG. 5). Therefore, even small amounts of cathodal current not capable of reaching deep layers can still induce enough trigger area in MCs axonal arbor. Note that because MCs are unmyelinated, they do not require a large trigger area for activation. In contrast, for stronger current magnitudes, a similar probability of MCs activation is induced by anodal or cathodal stimulation. In fact, larger currents reach deeper layers, where the overall axonal arborization of MCs also includes vertical fibers. This results in a chance for anodal stimulation to trigger activation, and hence to have effects comparable to cathodal stimulation of the same magnitude. Layer I interneurons are characterized by horizontally oriented axonal fibers, which is very similar to MCs. Therefore, their activation probability should depend on cathodal current in a very similar trend as MCs.

Bitufted cells from LII/III do not clearly fit in one of the categories described above. In particular, the probability dependence on the current magnitude for anodal stimulation of bitufted cells is very similar to the one of MCs from layer V, but not for cathodal stimulation. This is likely because bitufted cells are unmyelinated (as MCs) and have vertical axonal fibers close to their somas (as MCs). Therefore, the same interaction of arborization shape and current magnitude applies to bitufted cells and MCs in the case of anodal stimulation. Conversely, the lack of horizontally oriented axonal fibers in bitufted cells (as compared to MCs) prevents cathodal stimulation from activating bitufted cells as strongly as it activates MCs.

Various embodiments can be used to predict multiple currents to trigger population response and a strong difference for anodal and cathodal stimulations. The above-described embodiments focused on direct activation of individual cortical neurons by the stimulation current. However, various embodiments can ignore the fact that these neurons can be synaptically connected. Accordingly, various embodiments can predict an overall network response using a computational model of the cortical column receiving surface cortical stimulation. Embodiments of this are now described. In various embodiments, the axonal density may be computed as follows: first, all 3D reconstructions of cells of a certain type are aligned in space and centered at the soma, such that axis coordinates (x, y, z) correspond to width, height and depth of the slice respectively. Second, all reconstructions can be superimposed in a 3d volume, and the axonal density constructed on a grid of a size 100 points in the x direction, by 100 points in the y direction, by 50 points in the z direction. Finally, the 3D density array can be averaged across the z-axis and the result plotted. The example of FIG. 6B is plotted in a logarithmic scale.

Figure 11:
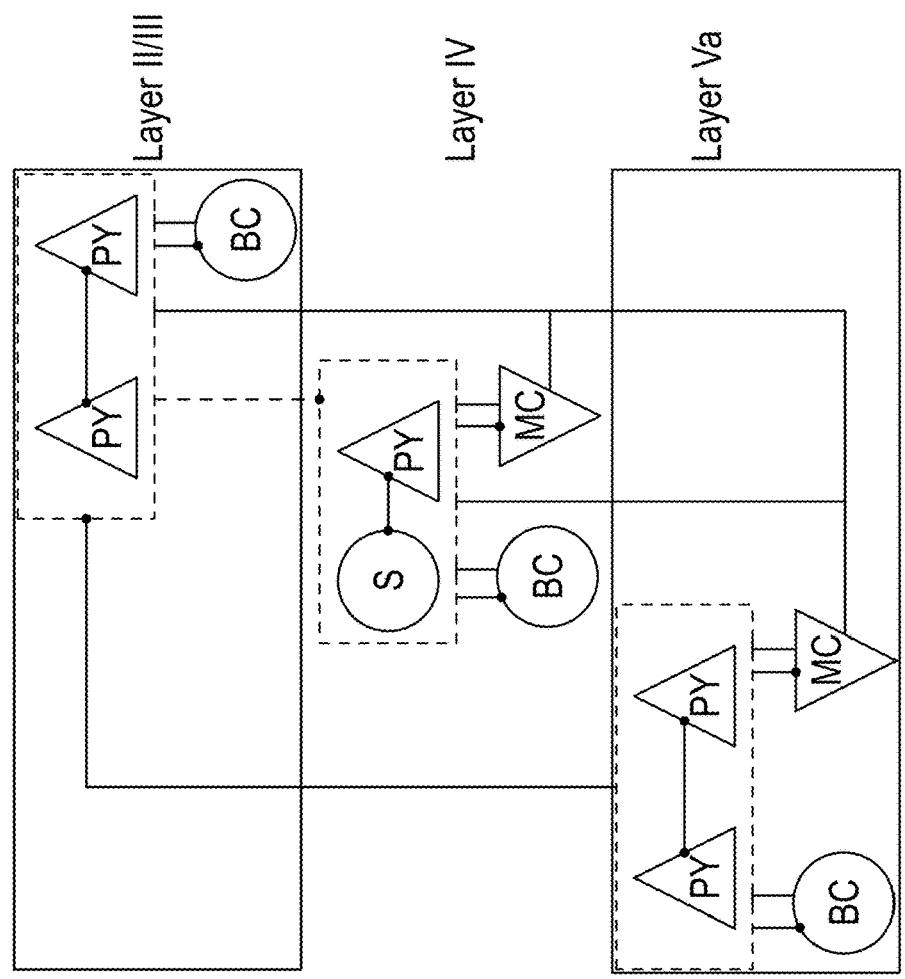
FIG. 11 is a diagram illustrating an example of the overall connectivity of a network model structure for a simple computational model of the cortical column receiving surface cortical stimulation in accordance with one embodiment of the present disclosure.

In one embodiment, the cortical model included excitatory neurons (PYs and SCs) and inhibitory interneurons (BCs and MCs), but omitted the other interneuron types because of their low density. The neurons in the model can include probabilistic synaptic connections, organized according to canonical microcircuit architecture. FIG. 11 is a diagram illustrating an example of the overall conductivity of the network. This illustrates a network model structure having three types of cells located in three different layers (canonical circuit). In this example, PY stands for pyramidal neuron, SpS stands for spiny stellate cell, BC stands for basket cells, and MC stands for Martinotti cells. Lines with circles denote excitatory AMPA connections (solid—strong, dashed—weak), whereas bars denote inhibitory GABA connections. In this example, all excitatory cells within each layer have recurrent excitatory connections, (b) PYs and SCc from layers IV and Va had strong projections to PYs from layers II/III, (c) BCs formed strong inhibitory connections to excitatory neurons within their own layers, and (d) MCs from layers IV and V made cross-layer inhibitory connections specifically targeting excitatory cells in layer IV.

Figure 12:
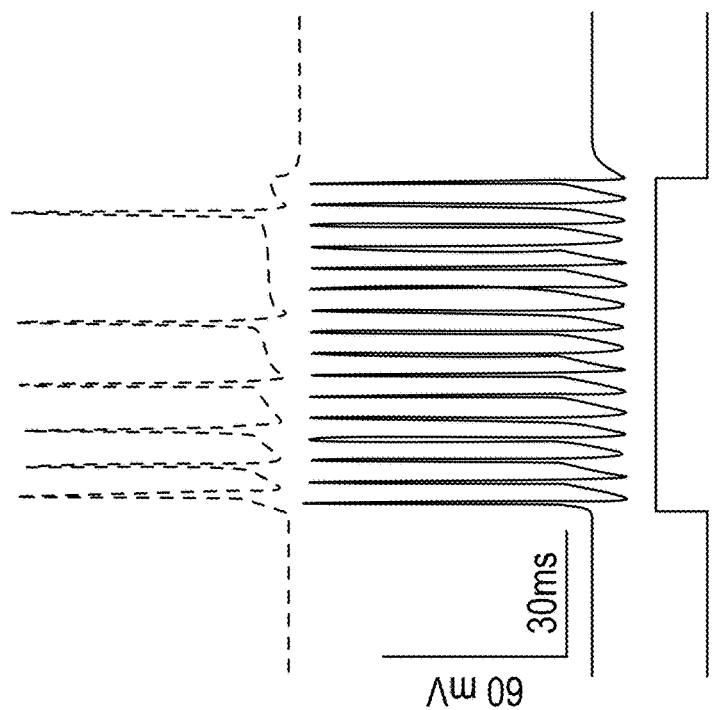
FIG. 12 illustrates voltage traces for spiking neurons in the example model of FIG. 11.

Two electrophysiological classes of neurons are used in this embodiment: regular spiking neurons to represent PYs, SCs and MCs and fast spiking interneurons to represent BCs. An example of this is shown in FIG. 12, which illustrates voltage traces for the spiking neurons. Particularly, this shows two electrophysiological classes of neurons that can be used in various embodiments. The top voltage trace corresponds to regular spiking neurons (e.g., used for pyramidal, spiny stellate cells and Martinotti cells) and the bottom voltage trace demonstrates activity of fast spiking interneurons (e.g., used for basket cells).

In various embodiments, all inhibitory interneurons had lower leak current, which resulted in a higher responsiveness of these cells in comparison to excitatory neurons. Without input, the neurons may be assumed to remain silent. For the first 5 ms (a duration consistent with experimental protocols), all cells may be activated according to the probabilities estimated from the analysis (e.g., as shown in FIGS. 9, 10A-I).

Figure 13:
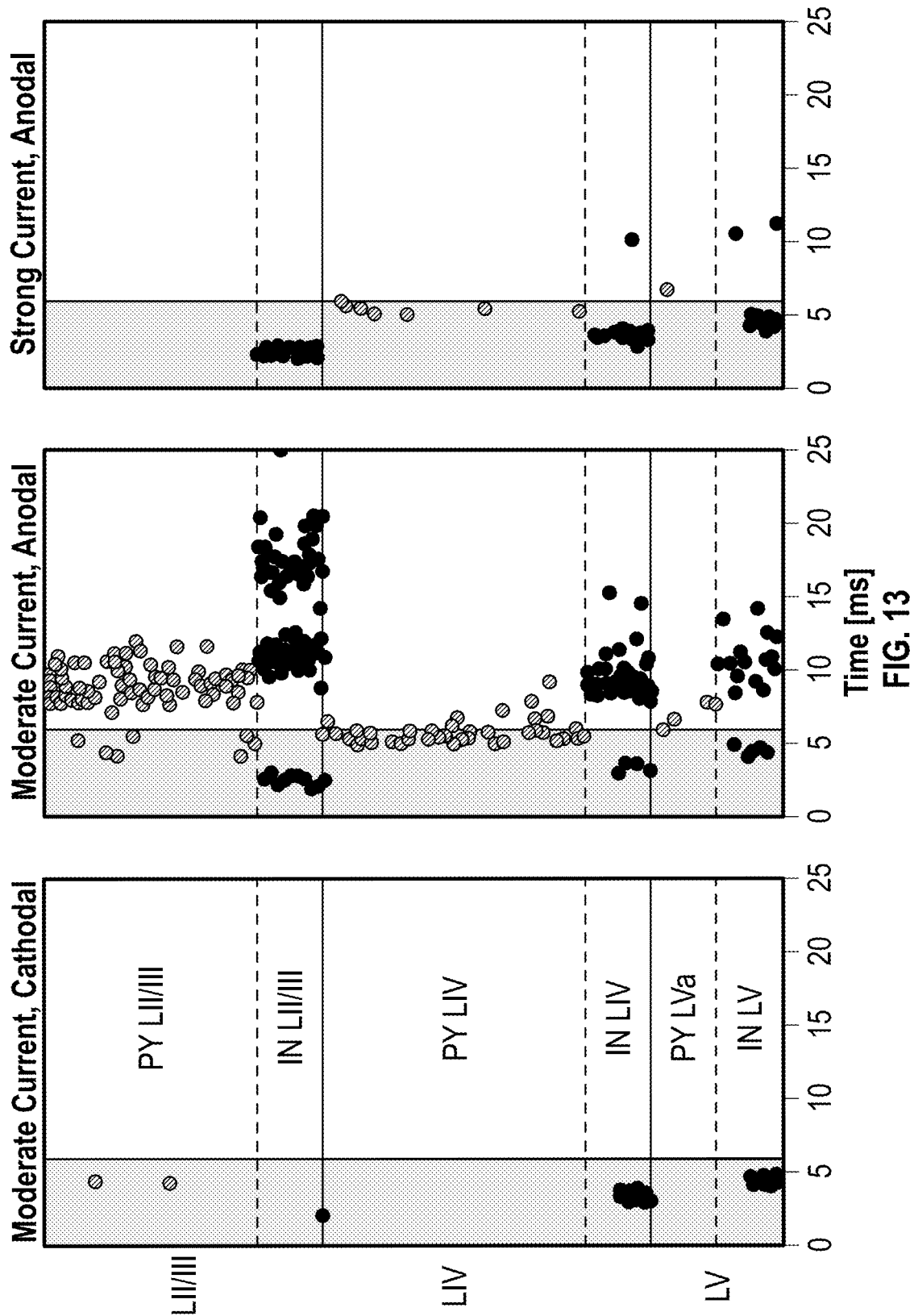
FIG. 13 shows representative examples of the network response to moderate and strong magnitudes of surface current stimulation in the example model.

The model was tested for different types (anodal vs cathodal) and magnitudes of current stimulation. When current magnitudes were low, the probability of direct activation was low (e.g., FIG. 10A-C). In the network, this led to the sparse spiking in few pyramidal cells and inhibitory interneurons. However, no lasting population response was evoked (data not shown). FIG. 13 shows representative examples of the network response to moderate and strong magnitudes of surface current stimulation. Particularly, the three panels compare the activity elicited in cells by different types of stimulation (cathodal in left panel, and progressively larger anodal stimulation in the two right panels). Spike raster plots exhibit network activity for cathodal (left panel) and anodal (two right panels) stimulations. Gray shading denotes the stimulation period (5 ms, see text). This shows PY and SpS cell spikes, and interneuron spikes. The left panel shows a weak response to cathodal stimulation (−100 μA). The middle panel shows response to moderate anodal stimulation (75 μA), which induced a large population response. The right panel shows response to a strong positive current (300 μA), which activated a large number of basket cells in layer II/III and Martinotti cells in all layers, which prevented the activation of excitatory cells in layers II-IV.

The left panel in FIG. 13 shows the network response to moderate cathodal stimulation. The estimate revealed that cathodal stimulation triggered spiking in a smaller number of PY in LII/III, but activate a larger number of MCs and layer I interneurons in comparison to anodal stimulation. Therefore, this leads to the hypothesis that cathodal stimulation can recruit strong inhibition in the tissue below the electrode, and produce weaker overall response. When tested in simulations, this hypothesis held true. In fact, cathodal stimulation evoked spikes in a large number of MCs in all layers, including LIV and V where they constitute a large fraction of all interneurons. Note that MCs from infragranular layers specifically target excitatory cells in LIV. Therefore, the effective recruitment of inhibition and relatively small activation probability of LII/III PYs resulted in a weak and sparse response of excitatory cells in our model column (left panel in FIG. 13).

The middle panel of FIG. 13 shows that anodal stimulation of the intermediate intensity could trigger network activity across the layers for a considerable period after stimulus offset. In fact, stimulation triggered abundant spiking in mutually excitatory PYs and SCs in LIV, and some spikes in PYs in LII/III. In turn, the connectivity within LIV created reverberating excitatory activity that promoted a strong local network response, which projected onto LII/III PYs, eliciting a strong population response within L II/III. While activity of PYs in layers IV and II/III did outlast the duration of current input, it also recruited feedback inhibition from BCs and MCs, leading to termination of the response activity. The simulations show that anodal currents of moderate magnitudes can induce a functional response beyond the stimulation duration and location. In fact, firing of LII/III PYs had the potential to reach other columns and deep layers PYs, which could then transmit to other areas the activity elicited in the network by the brief surface stimulus.

In the case of strong anodal stimulation, the estimates showed a high probability of activation for most cell types (FIG. 10A-C). Once connected, the simulations predicted a network response dominated by inhibitory activity (FIG. 13, right panel). In fact, current stimulation activated both interneurons and excitatory cells, but the larger input resistance and higher responsiveness of interneurons compared to PYs and SCs resulted in the activation of these inhibitory neurons before the spikes in excitatory cells. Because of the large number of interneuron spikes evoked, synaptic inhibition on PYs and SCs could overcome the excitatory drive due to stimulation, and effectively stopped them from firing. Because of the lack of directly recruited inhibition in layer Va, slender-tufted PYs were activated by stimulation, but their relatively low density meant that they could only deliver a small amount of excitation to the highly inhibited upper layers.

Figures 14A, 14B:
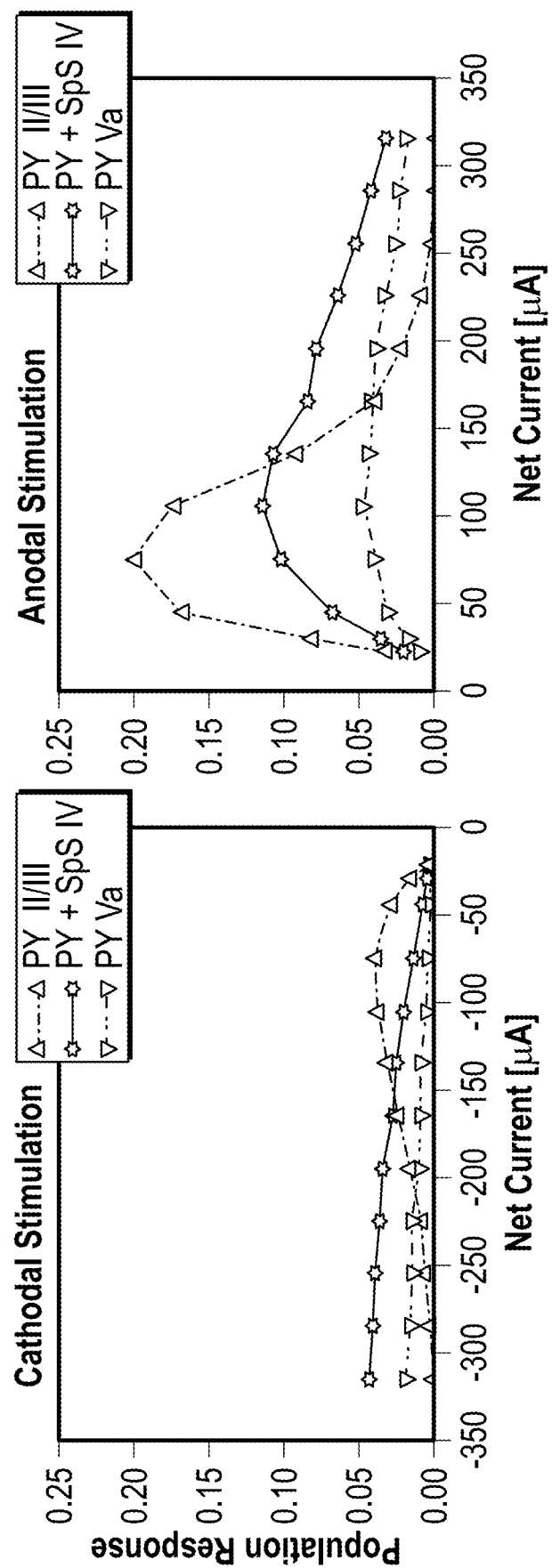
FIG. 14A illustrates population responses for cathodal stimulation as a function of net electrode current for layer II-IV excitatory cells in the example model.
FIG. 14B illustrates population responses for anodal stimulation as a function of net electrode current for layer II-IV excitatory cells in the example model.

While FIG. 13 shows few characteristic examples, FIG. 14A and FIG. 14B illustrate a summary of the findings across simulations with many current magnitudes. The plots in FIG. 14A and FIG. 14B show the average population response (computed as a number of spikes divided by the total population number) for excitatory cells as a function of applied stimulation current I (cathodal in FIG. 14A and anodal in FIG. 14B). For low current, probability of direct activation was low in both anodal and cathodal stimulations, whereas for large current, inhibitory activity suppressed spiking in PYs and SCs. Importantly, for excitatory cells and anodal stimulation there was an optimal range of stimulation current magnitudes where population response was highest (consistent with our description of network dynamics in FIG. 13, middle panel). In fact, the input evoked moderate amount of excitatory spiking amplified by recurrent excitation, which led to the high overall response in the cortical column.

The foregoing describes examples by which the probability of activation for different cell types and in different cortical layers can be estimated when exposed to external electrical stimulation. Example embodiments included a finite size electrode of known geometry placed on the cortical surface. The approach included four main steps: first, estimating the electric field potential in the tissue; second, defining the 'axonal-electrical receptive field' based on reconstructions of different cell types across the layers; third, estimating the cells' spiking probability based on the activation function in axonal elements; and fourth, predicting the network response to stimulation in a minimal model of a cortical column based on the spiking probability estimates. Experimental data indicates that short-lived superficial stimulation with a single electrode source has the ability to trigger spiking in layer IV pyramidal cells, and to evoke network activity that could persist for hundreds of milliseconds. It further indicates the likelihood of a much higher spiking response to anodal stimulation compared to cathodal one, as well as existence of the optimal stimulation intensity, capable of inducing a maximal response in a population of cortical cells.

The systems and methods described herein can be useful in a number of applications. Recent advances in techniques of multisite cortical stimulation aimed at restoring damaged brain operations like movement, sensation, perception, memory storage and retrieval, underscore the need for better understanding of the effects of such stimulation on individual neurons and synaptic connections. Embodiments disclosed herein may employ local electrical stimulation that may elicit activity under a superficial electrode sufficient to enable signal transmission without trumping the physiology of the network.

In further embodiments, stimulation within an intermediate range of positive input currents (anodal stimulation) may trigger network response that survives the end of the stimulus, and thus can potentially be similar to the physiological processing in the stimulated tissue. This can be important if the stimulation is intended to induce physiologically relevant persistent changes in brain tissue. For example, inducing synaptic plasticity is necessary for stimulation to be successful as an intervention to restore memories, promote the recovery of a cortical area lost functions, or repress hyper-excitability of a portion of tissue. But blanket plasticity evoked by the cell spiking that is directly triggered by external current is not likely to match existing synaptic patterns and will not have any meaningful constructive impact on a system of careful counter-balances like the brain. In contrast, stimulating in the range of currents that elicit network-driven activity that continues when the stimulus is removed provides a better chance for stimulation to be changing only a selected and physiologically meaningful subset of synapses. In other words, there is a range of current values in which stimulation can be used as a sophisticated and detailed intervention rather than a blunt hammer, and such range can be found combining theoretical estimates of the current density and reconstructed anatomy.

It is generally understood that electrical microstimulation directly activates axon initial segments and nodes of Ranvier, which are the most excitable elements due to the high concentration of sodium channels. Thus, the estimation of direct activation of cortical cells in various embodiments is based on calculation of the activation function along the axonal segments. This approach takes into account orientation and thickness of axons, and also considers their myelination properties. Some embodiments define a threshold for the effective stimulation current in an axonal segment (given by the activation function) by direct comparison to the experimental data: in turn, this threshold enables the calculation of cell activation probability. Various embodiments apply the same method to excitatory and inhibitory populations, which implies that all parameters of the estimation scheme (such as threshold for activation function) are the same for all cells. Because BCs have higher input resistance compared to PYs, it is possible that their experimental threshold could be lower than the estimate. However, this should not affect the conclusions: in fact, the suppression of excitatory firing at high input current values would still hold, because it hinges on BCs spiking before PYs (which would only be enhanced by lowering the threshold).

It should be noted that inhomogeneity in the tissue would affect the trigger area along axons, and could change activation properties in each particular cell. However, because embodiments of the systems and methods disclosed herein estimate averages across cell rotations, shifts and multiple different reconstructions to compute a probability of spiking. This implies that the effect of local changes in the tissue (e.g., such as those driven by inhomogeneity) would likely affect the final average probability only marginally. Accordingly, these methods should not result in the emergence of dramatically different estimates for cell activations from finer estimates of tissue properties.

The connectivity within the described example network model was based on the canonical model, which captures the main picture of the information flow across cortical layers. For simplicity, this model ignores finer properties like the descending projections from excitatory to inhibitory neurons, the activity of less frequently observed interneurons (bi-tufted, neuroglia form, etc.), the fine variability of pyramidal cells within layer II/III PYs and their projections. Also, the network model predictions can be extended toward multi-compartment neuronal models, which can take into account finer structure of inhibitory targeting (e.g. tuft vs soma-targeting interneurons) and explicitly model propagation of orthodromic and antidromic spikes.

Embodiments can provide estimates based on the activation function without considering the voltage dynamics within axonal trees. However, theoretical work addressing axonal dynamics through multi-compartmental modeling has shown that for moderate currents, the activation function correlates with voltage dynamics and predicts the activation sites within axonal elements. For very strong currents, areas along axonal arborization could be inactivated, blocking propagation of action potential along the axon. In this case, various embodiments may render inadequate results. However, the blocking phenomenon arises only for relatively strong stimulation currents and typically affects elements that are very close to the electrode. Hence, for small stimulation currents and superficial electrode configuration, the blocking phenomenon should not qualitatively change the results. Overall, the details of axonal propagation dynamics are not essential because various embodiments focus on average estimates of response for a cell type, rather than an account of stimulation-induced dynamics in a specific cell.

While various embodiments disclosed herein applied the microstimulation protocol by a single superficial electrode, these can be directly generalized to a number of more complex settings by using linear summation and adjusting the calculations for the current density: multiple electrodes (as in ENIAC), in-depth stimulation (as in epilepsy), non-circular electrode plates (as in DCS) and bi-polar electrodes (as in DBS) can all be accounted for. Also, although various embodiments assume a generic cortical tissue volume, the same approach can be applied to the tissue different from a canonical cortical column (e.g., hippocampus, geniculate nuclei, damaged tissue after traumatic brain injury or stroke) as long as enough data on reconstructed cells are available.

Because different stimulation protocols use different current waveforms, it is important to note that this approach can be generalized to the other stimulation protocols as long as an activation threshold has been experimentally measured. The type of activity elicited by stimulation can also be expanded. Systems and methods disclosed herein are in some cases presented in the context of evaluating activation mediated by axonal spikes, an effect relevant for fast and strong stimulation protocols (ENIAC, DBS), but other types of stimulation could be focused on triggering subthreshold effects, such as voltage polarization at somas compared to dendrites (tDCS). The methods can be adapted to account for these sub-threshold effects such as, for example, by embedding the reconstructed cells in the electric field and considering a probability of depolarization/hyperpolarization, taking into account the specific orientation of each element of the reconstructed cell compared to the direction of the current field.

Embodiments of the systems and methods disclosed herein can provide a generic approach to estimating probabilities of cell activation in response to external stimulation, and applied to make testable predictions regarding the effects of superficial electrical microstimulation of a canonical cortical circuit. Ongoing rapid extension of the available data on the reconstructed neuronal anatomy will enable increases in the precision of the analysis and application to other brain regions and species.

Various methods can be used for estimating electric potential for a single electrode. In one embodiment, it is assumed that the current delivered by the stimulation electrode (I) is a fixed amount. As noted above, embodiments consider a cartesian coordinate system (X,Y,Z) centered at the electrode, where the Z axis is oriented perpendicular to the electrode surface and extends in depth across cortical layers. The X and Y axes are oriented parallel to the surface and electrode plate (e.g., see FIG. 1). To a first approximation, the current I across the insulating layer of the electrode can be assumed to be uniform over the electrode surface. Each infinitesimally small element of the electrode dS then produces a current source as:

$$dI = \frac{IdS}{S} = \frac{I}{S}dxdy$$

where S is the electrode surface, dS=dxdy is the infinitesimal electrode element. Here, the pair (x, y) locates the current source on the surface of the circular electrode (where Z=0). The elemental current source produces a tissue potential at distance L from the source given by:

$$d\Phi = \frac{\rho_e I}{4\pi S} \frac{dxdy}{L}$$

where ρe is the conductivity of the tissue, S=A2 is the surface area of the electrode, A is the electrode radius and/is the total current generated by the electrode.

Note that the distance can be expressed as $$L=\sqrt{(X-x)^2+(Y-y)^2+Z^2}.$$

Accordingly, the potential in the Cartesian coordinate system (X,Y,Z) is given by $$\Phi(X,Y,Z) = \frac{\rho_e I}{4\pi A^2} \int\int_{-A/2}^{A/2} \frac{dxdy}{\sqrt{(X-x)^2+(Y-y)^2+Z^2}}$$

The integral form of this equation is due to the need to compute the contribution of the entire electrode surface area A as a source of electrical current. However, at large distances the finite size of the electrode has a nominal effect on the electrical field. In such conditions, the electrode can be represented as a point source of current, leading to the following approximation of the potential field:

$$\Phi(X,Y,Z) = \frac{\rho_e I}{4\pi\sqrt{X^2+Y^2+Z^2}}$$

According to one-dimensional cable theory, the dynamics of transmembrane voltage of axonal segments can be computed as follows:

$$\frac{c_m dV_i}{dt} = \left[\frac{d}{4\rho_i}\left(\frac{V_{i-1}-2V_i+V_{i+1}}{\Delta x^2} + \frac{\Phi_{i-1}-2\Phi_i+\Phi_{i+1}}{\Delta x^2}\right) - \sum I_n^{ion}\right]$$

Where Vi−1, Vi, Vi+1 denote transmembrane voltages of the neighboring axonal compartments (subindex denotes number of the compartment), cm=1 μF cm² is a capacitance of membrane per square unit area, d stands for diameter of the axon (typically between 10 μm and 1 μm), ρi=300 Ω·cm is a resistivity of axoplasm, Δx is a discretization parameter, which defines length of the compartment. The term $\Sigma I_n^{ion}$ describes the sum of intrinsic ionic current such as fast potassium and sodium currents for spike generation, leak currents and others. As one can see, the effective transmembrane current, which arises due to extracellular electrical stimulation is described by the term $$f = \frac{d}{4\rho_i}\frac{\Phi_{i-1}-2\Phi_i+\Phi_{i+1}}{\Delta x^2}$$

where $\phi_i$, $\phi_{i-1}$, $\phi_{i+1}$ stand for extracellular potentials in the vicinity of axonal compartments. In fact, $f$ represents activation function (26) and in the limit Δx→0 can written as $$f = \frac{d}{4\rho_i}\frac{\partial^2 \Phi}{\partial x^2}$$

(here axis x represents direction of axonal fiber). The activation function (computed along reconstructed axons) can be used to estimate probability of axonal activation.

Publicly available resources for neuronal morphologies can be used to obtain cell reconstructions. Examples of these are shown in Table 1. Cell reconstructions can be corrected for tissue shrinkage and aligned when necessary. The overall data set need not be homogenous because cells can be obtained from distinct experiments. However, for cell types, the parameters can be adjusted in order to account for possible differences in thickness of the cortex and cell sites. Accordingly, embodiments can estimate approximate boundaries for each layer and use those values in statistical analysis to predict activation probability. The variations tend to be small or negligible, however.

TABLE 1

Summary of datasets with reconstructed cells.

| Cell type | Size of dataset | Srtain (Age) |
|---|---|---|
| Pyramidal cells (II/III) | 26 | Wistar (P20-25), Sprague Dawley (25-36) |
| Pyramidal cells (IV) | 33 | Wistar (P19-21), Sprague Dawley (25-36) |
| Slender-tufted PYs (Va) | 43 | Wistar (P20-21), Sprague Dawley (25-36) |
| Thick-tufted PYs (Vb) | 30 | Wistar (P14) |
| Spiny stellate cells (IV) | 9 | Wistar (P19-21) |
| Layer I interneurons | 118 | Wistar (P13-16) |
| Basket cells (II/III) | 97 | Wistar (P13-15) |
| Basket cells (IV) | 83 | Wistar (P13-15) |
| Basket cells (V) | 58 | Wistar (P13-15) |
| Martinotti cells (II/III) | 13 | Wistar (P13-16) |
| Martinotti cells (IV) | 9 | Wistar (P13-16) |
| Martinotti cells (V) | 7 | Wistar (P13-16) |
| Bi-tufted cells (II/III) | 18 | Wistar (P13-15) |
| Bi-tufted cells (IV) | 6 | Wistar (P13-15) |
| Bi-tufted cells (V) | 11 | Wistar (P13-15) |

Computations of the averaged probability of activation may be based on the calculation of the activation function and the trigger area. The trigger area comprises axonal segments with sufficiently high (e.g., above 3 pA/μm²) values of an activation function, which can initiate axonal action potential in unmyelinated segments of axons (e.g. nodes of Ranvier). The threshold may be defined based on comparisons to experimentally recorded current-distance relations for pyramidal cells. Note that this threshold may be computed for axon initial segment, but embodiments can use the same value for nodes of Ranvier. For unmyelinated fibers, embodiments may assume a 20-fold larger threshold, since their excitability is lower due smaller concentration of sodium channels.

To compute the averaged probability for a certain class of cells (Table 1) located at distance $R_0$ from the electrode embodiments can apply following steps.

As a first step, one of the anatomical reconstructions may be placed at a distance $R_0$ from the electrode at a certain depth Z within the layer to which the cell belongs.

Next, the activation function $f$ can be computed for axonal segments of the reconstructed cell. The function may be evaluated against the threshold (3 pA/μm² for myelinated and 60 pA/μm² for unmyelinated fibers). The segments that possess a large (above threshold) activation function may be marked as a trigger area, whose elements may initiate axonal response.

The length of the trigger area L may be transformed into a probability of spiking. For myelinated fibers, the trigger area should contain at least one node of Ranvier to initiate axonal response. Hence, the overall probability p of response for myelinated axon can be estimated as $$p = 1 - \left(\frac{D-k}{D}\right)^{L/k},$$

where D denotes the averaged internodal distance (e.g., 100 μm may be used in all estimations) and k denotes the length of node of Ranvier (e.g., 1 μm may be used in all estimations). For unmyelinated fibers, whose entire membrane is exposed to extracellular space, a binary dependence of probability on L may be assumed. For example, for any L>0 (presence of trigger area) produced activation can be assumed, while the absence of trigger area (L=0) can be assumed to mean no activation.

The foregoing steps may be repeated for various locations (different Z) and for various orientations of the cell. Note that cells tend to grow towards the surface and occupy a significant area in layer I. Therefore, in various embodiments, the depth coordinate Z varied in the range [$Z_{min}$, $Z_{min}$+$cL_S$], where $Z_{min}$ is a minimal possible depth of the soma, $L_s$ is a layer size and c is a coefficient (0.1 for all cells except basket cell, for which c=0.4). The minimal depth for a cell soma $Z_{min}$ is given by the upper boundary of the cell's layer for cell types that are compact (e.g. basket cells in infragranular layers, whose arborization does not reach the surface). For large cells, which show arborizations that can reach the cortical surface (e.g. all pyramidal cells), the $Z_{min}$ value is taken as the length from the soma to the highest point in ascending arbor, whether such branch is axonal or dendritic.

Combining the results from the above step yields an overall probability that a given cell reconstruction would be activated.

These steps may be repeated for every cell reconstruction from the pool of available neurons. The probability may be calculated averaging across all cells, to represent the overall likelihood of axonal activation for a given cell class at distance $R_0$ from the electrode.

It should be noted that the computational model of the canonical cortical circuit in various embodiments represents a cortical column, which contains pyramidal (PY), spiny stellate (SC), basket (BC) and Martinotti (MC) cells from layers II-V. Note that there is a large diversity of different types of interneurons in the cortex, but embodiments may be restricted to the most common and the most important types. BCs constitute about 50% of all interneurons in the cortex and form a major source of lateral inhibition within the layers. MCs are likely to be activated in all layers due to their specific form of axonal arborization. Moreover, MCs comprise a significant part of all interneurons in infragranular layers where they specifically target excitatory cells in layer IV. Excitatory neurons (PYs and SCs) and inhibitory MCs were modeled as regular spiking cells with spike rate adaptation (e.g., FIG. 12, top voltage trace shown for PYs), whereas inhibitory BCs were modeled as fast spiking cells (FIG. 12, middle voltage trace). Interneurons may exhibit a lower leak current, which results in a higher responsiveness in comparison to the excitatory cells. Cell dynamics is governed by Hodgkin-Huxley-type kinetics, which includes fast Na+-K+ spike generating mechanism (for all types of cells), high-threshold activated Ca2+ current (for PY and SCs) and slow calcium-dependent potassium (AHP) current (for regular spiking cells).

The following equations are also useful for the systems and methods disclosed herein. The membrane potential is governed by the following equation:

$$C_m \frac{dV_i}{dt} = I_{ion}(V_i) + I_i^{syn} + I_i^{ext} + \eta \xi_i;$$

The ionic currents $I_{on}(V_i)$, which are responsible for intrinsic cells dynamics, read:

$$I_{ion}(V_i) = g_{Na} m_i^3 h_i (V_{Na} - V_i) + g_K n_i^4 (V_K - V_i) + g_L(V_L - V_i) +$$
$$g_{Ca} \frac{V_{Ca} - V_i}{1 + \exp(-(V_i - V_{th})/V_{shp})} + g_{ahp} \frac{c_i}{c_i + k_d}(V_K + V_i)$$

The gating variables $m_i$, $n_i$, $h_i$ evolve according to:

$$\frac{dx_i}{dt} = \alpha_x(V_i)(1 - x_i) - \beta_x(V_i) x_i,$$

where $x_i$ is one of gating variables. The functions $\alpha_x(V)$ and $\beta_x(V)$ are:

$$\alpha_m(V) = \frac{0.32(54 + V)}{1 - \exp(-0.25(V + 54))},$$

$$\beta_m(V) = \frac{0.28(V + 27)}{\exp(0.2(V + 27)) - 1},$$

$$\alpha_h = 0.128 \exp\left(-\frac{50 + V}{18}\right),$$

$$\beta_h = \frac{4}{1 + \exp(-0.2(V + 27))},$$

$$\alpha_n = \frac{0.032(V + 52)}{1 - \exp(-0.2(V + 52))},$$

$$\beta_n = 0.5 \exp\left(-\frac{57 + V}{40}\right).$$

Calcium concentration $c_i$ obeys the following equation:

$$\frac{dc_i}{dt} = -\alpha_{Ca} g_{Ca} \frac{V_i - V_{Ca}}{1 + \exp\left(-\frac{V_i - V_{th}}{V_{shp}}\right)} - \frac{c_i}{\tau_{Ca}}$$

and governs calcium-dependent hyperpolarizing potassium current $$I_{AHP} = g_{ahp} \frac{c_i}{c_i + k_d}(V_K - V_i),$$

which is responsible for spike-frequency adaptation.

The synaptic input may be modeled according to:

$$I_i^{syn} = \Sigma_j G_{ij}^{exc} s_j^{exc}(v_{syn}^{exc} - V_i) + \Sigma_j G_{ij}^{inh} s_j^{inh}(V_{syn}^{inh} - V_i)$$

where synaptic variables $s_j^{exc,inh}$ sjexc,inh are governed by the following equation:

$$\frac{ds_j}{dt} = \alpha_s^{exc,inh} S(V_j)\left(1 - s_j^{exc,inh}\right) - \beta_s^{exc,inh} V_j$$

The function S(V) reads:

$$S(V) = \frac{1}{1 + \exp(-100(V - 20))}.$$

The term $I_i^{ext}$ denotes applied external current (stimulus that leads cells to spike during stimulation), and the term $\eta\xi_i(t)$ corresponds to the fluctuations in the afferent input (representing spontaneous background activity), which are given by a white noise process with the following properties: $<\xi_i(t)>=0$, $<\xi_i(t)\xi_i(t-t_0)>=\delta(t-t_0)$. Here $\delta(t)$ stands for Dirac delta function, the constant $\eta$ determines the strength (standard deviation) of the noise.

The following summarizes all parameters of the individual cells and network architecture used in the described model:

Parameters that were Common Across all Cell Types:
$V_K$=−100 mV, $V_{Na}$=50 mV, $V_{Ca}$=120 mV, $V_{shp}$=2.5 mV, $V_{th}$=25 mV, $C_m$=1 μF/cm², τCa=200 ms⁻¹, $\alpha_{Ca}$=0.005, $a_s^{exc}$=0.6 ms⁻¹, $\beta_s^{exc}$=0.2 ms⁻¹, $a_s^{inh}$=0.5 ms⁻¹, $\beta_s^{inh}$=0.1 ms⁻¹, $V_{syn}^{exc}$=0 mV, $V_{syn}^{inh}$=−80 mV, η=0.4.

Specific Parameters:
PYs and SCs:
$g_L$=0.6 mS/cm², $V_L$=−67 mV, $g_K$=2.5 mS/cm², $g_{Na}$=30 mS/cm²,
$g_{Ca}$=0.1 mS/cm², $g_{ahp}$=0.5 mS/cm².

MCs:
$g_L$=0.4 mS/cm2, $V_L$=−65 mV, $g_K$=10 mS/cm², $g_{Na}$=60 mS/cm²,
$g_{Ca}$=0.1 mS/cm², $g_{ahp}$=0.75 mS/cm².

BCs:
$g_L$=0.4 mS/cm², $V_L$=−65 mV, $g_K$=10 mS/cm², $g_{Na}$=60 mS/cm²,
$g_{Ca}$=0.0 mS/cm², $g_{ahp}$=0.0 mS/cm².
$g_L$=0.4 mS/cm², $V_L$=−65 mV, $g_K$=10 mS/cm², $g_{Na}$=60 mS/cm², =0 mS/cm²,
$g_{ahp}$=0.
Network Structure and Connectivity:
Structure:

| Type of cortical cells | Number of cells |
| --- | --- |
| PY II/III | 200 |
| BC II/III | 50 |
| PY + SC IV | 200 |
| BC IV | 25 |
| MC IV | 25 |
| PY Va (slender) | 50 |
| BC V | 25 |
| MC V | 25 |

PY—pyramidal neurons, BC—basket cells, SC—excitatory spiny stellate cells, MC—Martinotti cells.
Connectivity:

| To | From | Type | Strength | Probability |
| --- | --- | --- | --- | --- |
| PY, BC II/III | PY II/III | AMPA | 0.75 | 0.1 |
| PY II/III | PY, SC IV | AMPA | 1.5 | 0.05 |
| PY II/III | PY Va (slender) | AMPA | 0.75 | 0.05 |
| PY, SC, BC, MC IV | PY, SC IV | AMPA | 1.5 | 0.1 |
| PY, SC IV | PY II/III | AMPA | 0.25 | 0.05 |
| PY Va (slender) | PY Va (slender) | AMPA | 0.75 | 0.1 |
| BC, MC | PY Va (slender) | AMPA | 0.75 | 0.1 |
| PY II/III | BC II/III | GABA | 3 | 0.25 |
| PY II/III | MC IV, V | GABA | 0.5 | 0.05 |
| PY, SC IV | BC IV | GABA | 3 | 0.25 |
| PY, SC IV | MC IV | GABA | 3 | 0.25 |
| PY, SC IV | MC V | GABA | 2 | 0.2 |
| PY Va (slender) | BC V | GABA | 3 | 0.25 |
| PY Va (slender) | MC IV, V | GABA | 0.5 | 0.05 |

Figure 15:
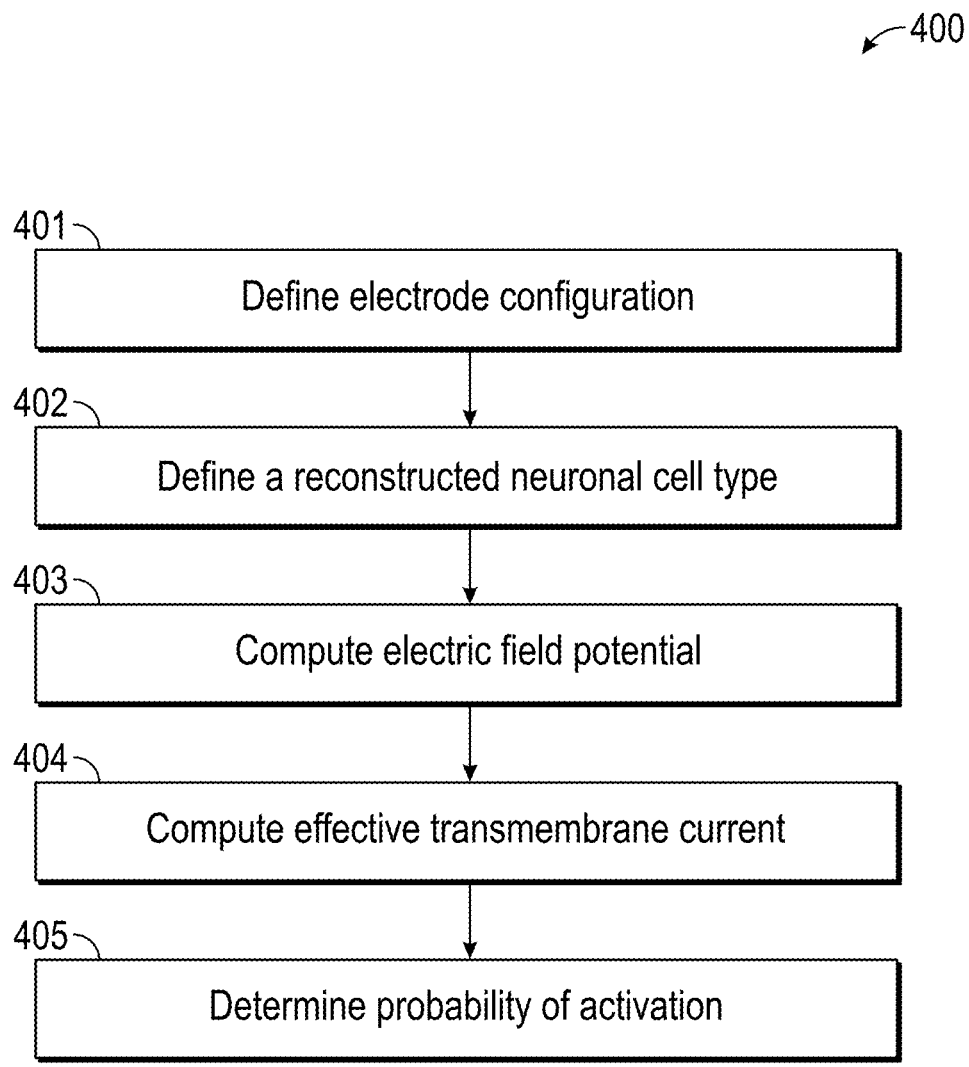
FIG. 15 illustrates a diagram for a method of determining the probability of activation for a reconstructed neuronal cell.

FIG. 15 illustrates a block diagram for a method 400 of determining the probability of activation for a stimulated neuronal cell according to the embodiments disclosed herein. According to present embodiments the method may comprise the step 401 of defining an electrode configuration of an electrode, wherein the electrode stimulates a reconstructed neuronal cell. As disclosed herein, defining the electrode configuration may comprise specifying a size, shape, and current output of the electrode. In step 402, the method may define a reconstructed neuronal cell type for the reconstructed neuronal cell. According to the present embodiments, the defined reconstructed neuronal cell type may comprise a physical property or an electrical property of the reconstructed neuronal cell, wherein the physical property may comprise an average axonal density of the reconstructed neuronal cell.

The method may comprise the step 403 of computing an electric field potential at the reconstructed neuronal cell due to the electrode using at least the defined electrode configuration. According to some embodiments disclosed herein, the electric field potential at the reconstructed neuronal may be used to compute an effective transmembrane current of an arborization of the reconstructed neuronal cell at step 404. In various embodiments, the electric field potential may be computed at a position (R,Z) of the reconstructed neuronal cell relative to the electrode, wherein R is the planar distance from the center of the electrode and Z is the depth of the reconstructed neuronal cell within a type-defining cortical layer. In other embodiments, the effective transmembrane current may be described by an activation function for the reconstructed neuronal cell.

The method may comprise the step 405 of determining the probability of activation of the reconstructed neuronal cell using at least the computed effective transmembrane current and the defined reconstructed neuronal cell type. As disclosed herein, the average probability of activation may be determined for multiple reconstructed neuronal cells across multiple layers of cortical tissue. In such embodiments, an overall brain network response may be determined for any given electrode stimulation. In some embodiments, determining a probability of activation may comprise identifying a trigger area, wherein the trigger area comprises axonal segments of the reconstructed neuronal cell that possess activation function values above a threshold value. In such embodiments, the probability of activation for the reconstructed neuronal cell may be calculated using the length of the trigger area. In some embodiments, the steps of method 400 may be repeated for multiple reconstructed neuronal cells in a brain region, wherein the multiple reconstructed neuronal cells each have a respective reconstructed neuronal cell type. In such embodiments, the method may use statistical inference to predict an average response in a brain region for the multiple reconstructed neuronal cells.

According to embodiments disclosed here in, the described method may be performed by a non-transitory computer-readable medium, wherein the instructions, when executed by the processor, performs the steps of method 400.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. It will be apparent to one of skill in the art how alternative functional, logical or physical partitioning and configurations can be implemented to implement the desired features of the technology disclosed herein. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method of computing a probability of neuronal cell activation, comprising:
    a) defining an electrode configuration of an electrode, wherein the electrode configuration comprises an electrode plate adapted to communicate with a reconstructed neuronal cell through a skull, and wherein the electrode plate stimulates the reconstructed neuronal cell by generating an electrical current;
    b) computing, by a processor, an electric field potential at a position (R,Z) of the reconstructed neuronal cell relative to the electrode, wherein R is the planar distance from the center of the electrode and Z is the depth of the reconstructed neuronal cell within a type-defining cortical layer;
    c) using at least the computed electric field potential to compute an activation function for axonal segments of the reconstructed neuronal cell;
    d) identifying a trigger area, wherein the trigger area comprises axonal segments of the reconstructed neuronal cell that possess activation function values above a threshold value; and
    e) computing the probability of reconstructed neuronal cell activation using at least a length of the trigger area.

2. The method of claim 1, further comprising:
    reorienting the reconstructed neuronal cell;
    repeating steps (a)-(e) for the reoriented reconstructed neuronal cell; and
    calculating an overall probability of activation, wherein the overall probability of activation is based on at least on the probability of the reconstructed neuronal cell activation and the probability of the reoriented reconstructed neuronal cell activation.

3. The method of claim 2, wherein reorienting the reconstructed neuronal cell comprises at least one of:
    rotating the reconstructed neuronal cell; and
    vertically shifting the reconstructed neuronal cell.

4. The method of claim 3, wherein the vertical shifting of the reconstructed neuronal cell occurs within the range $[Z_{min}, Z_{min}+cL_s]$, where $Z_{min}$ is a minimal possible depth of the reconstructed neuronal cell soma, $L_s$ is a cortical layer size, and c is a coefficient.

5. The method of claim 1, where in the threshold value is determined experimentally by matching a current-distance relationship that leads to a direct activation of the reconstructed neuronal cell from an electrical stimulation.

6. The method of claim 1, wherein the activation function is represented by the equation:

$$f = \frac{d}{4\rho_i} \frac{\partial^2 \Phi}{\partial x^2}$$

where x represents the direction of an axonal fiber;
$\Phi$ is a function representing extracellular potentials in the vicinity of axonal compartments; and
$\rho_i$ represents a resistivity of axoplasm.

7. A system of computing a probability of neuronal cell activation, wherein the system comprises:
a memory; and
one or more processors, wherein the one or more processors are configured to execute machine readable instructions stored in the memory for performing the method comprising:
a) defining an electrode configuration of an electrode, wherein the electrode configuration comprises an electrode plate adapted to communicate with a reconstructed neuronal cell through a skull, and wherein the electrode plate stimulates the reconstructed neuronal cell by generating an electrical current;
b) computing an electric field potential at a position (R,Z) of the reconstructed neuronal cell relative to the electrode, wherein R is the planar distance from the center of the electrode and Z is the depth of the reconstructed neuronal cell within a type-defining cortical layer;
c) using at least the computed electric field potential to compute an activation function for axonal segments of the reconstructed neuronal cell;
d) identifying a trigger area, wherein the trigger area comprises axonal segments of the reconstructed neuronal cell that possess activation function values above a threshold value; and
e) computing the probability of reconstructed neuronal cell activation using at least a length of the trigger area.

8. The system of claim 7, wherein the one or more processors are configured to execute machine readable instructions stored in the memory for performing the method further comprising:
reorienting the reconstructed neuronal cell;
repeating steps (a)-(e) for the reoriented reconstructed neuronal cell; and
calculating an overall probability of activation, wherein the overall probability of activation is based on at least on the probability of the reconstructed neuronal cell activation and the probability of the reoriented reconstructed neuronal cell activation.

9. The system of claim 8, wherein reorienting the reconstructed neuronal cell comprises at least one of:
rotating the reconstructed neuronal cell; and
vertically shifting the reconstructed neuronal cell.

10. The system of claim 9, wherein the vertical shifting of the reconstructed neuronal cell occurs within the range $[Z_{min}, Z_{min}+cL_s]$, where $Z_{min}$ is a minimal possible depth of the reconstructed neuronal cell soma, $L_s$ is a cortical layer size, and c is a coefficient.

11. The system of claim 7, wherein the threshold value is determined experimentally by matching a current-distance relationship that leads to a direct activation of the reconstructed neuronal cell from an electrical stimulation.

12. The system of claim 7, wherein the activation function is represented by the equation:

$$f = \frac{d}{4\rho_i} \frac{\partial^2 \Phi}{\partial x^2}$$

where x represents the direction of an axonal fiber;
$\Phi$ is a function representing extracellular potentials in the vicinity of axonal compartments; and
$\rho_i$ represents a resistivity of axoplasm.

13. A non-transitory computer-readable storage medium storing a plurality of instructions executable by one or more processors, the plurality of instructions when executed by the one or more processors cause the one or more processors to:
a) define an electrode configuration of an electrode, wherein the electrode configuration comprises an electrode plate adapted to communicate with a reconstructed neuronal cell through a skull, and wherein the electrode plate stimulates the reconstructed neuronal cell by generating an electrical current;
b) compute an electric field potential at a position (R,Z) of the reconstructed neuronal cell relative to the electrode, wherein R is the planar distance from the center of the electrode and Z is the depth of the reconstructed neuronal cell within a type-defining cortical layer;
c) use at least the computed electric field potential to compute an activation function for axonal segments of the reconstructed neuronal cell;
d) identify a trigger area, wherein the trigger area comprises axonal segments of the reconstructed neuronal cell that possess activation function values above a threshold value; and
e) compute the probability of reconstructed neuronal cell activation using at least a length of the trigger area.

14. The non-transitory computer-readable storage medium of claim 13, wherein the plurality of instructions further cause the one or more processors to:
reorient the reconstructed neuronal cell;
repeat steps (a)-(e) for the reoriented reconstructed neuronal cell; and
calculate an overall probability of activation, wherein the overall probability of activation is based on at least on the probability of the reconstructed neuronal cell activation and the probability of the reoriented reconstructed neuronal cell activation.

15. The non-transitory computer-readable storage medium of claim 14, wherein reorienting the reconstructed neuronal cell comprises at least one of:
rotating the reconstructed neuronal cell; and
vertically shifting the reconstructed neuronal cell.

16. The non-transitory computer-readable storage medium of claim 15, wherein the vertical shifting of the reconstructed neuronal cell occurs within the range $[Z_{min}, Z_{min}+cL_s]$, where $Z_{min}$ is a minimal possible depth of the reconstructed neuronal cell soma, $L_s$ is a cortical layer size, and c is a coefficient.

17. The non-transitory computer-readable storage medium of claim 13, wherein the threshold value is determined experimentally by matching a current-distance relationship that leads to a direct activation of the reconstructed neuronal cell from an electrical stimulation.

18. The non-transitory computer-readable storage medium of claim 13, wherein the activation function is represented by the equation:

$$f = \frac{d}{4\rho_i} \frac{\partial^2 \Phi}{\partial x^2}$$

where x represents the direction of an axonal fiber;
$\Phi$ is a function representing extracellular potentials in the vicinity of axonal compartments; and
$\rho_i$ represents a resistivity of axoplasm.

* * * * *